United States Patent [19]
Sheldon

[11] Patent Number: 5,593,431
[45] Date of Patent: Jan. 14, 1997

[54] MEDICAL SERVICE EMPLOYING MULTIPLE DC ACCELEROMETERS FOR PATIENT ACTIVITY AND POSTURE SENSING AND METHOD

[75] Inventor: Todd J. Sheldon, Eagan, Minn.

[73] Assignee: Medtronic, Inc., Minneapolis, Minn.

[21] Appl. No.: 413,736

[22] Filed: Mar. 30, 1995

[51] Int. Cl.$^6$ .................................................. A61N 1/365
[52] U.S. Cl. ............................................................ 607/19
[58] Field of Search ................................... 607/2, 19, 18, 607/17

[56] References Cited

U.S. PATENT DOCUMENTS

| | | |
|---|---|---|
| 4,257,423 | 3/1981 | McDonald . |
| 4,374,382 | 2/1983 | Markowitz . |
| 4,428,378 | 1/1984 | Anderson . |
| 4,556,063 | 12/1985 | Thompson . |
| 4,869,251 | 9/1989 | Lekholm . |
| 5,010,893 | 4/1991 | Sholder . |
| 5,031,618 | 7/1991 | Mullett . |
| 5,127,404 | 7/1992 | Wyborny . |
| 5,226,413 | 7/1993 | Bennett . |
| 5,233,984 | 8/1993 | Thompson . |
| 5,318,596 | 6/1994 | Barreras . |
| 5,330,510 | 7/1994 | Legay . |
| 5,342,404 | 8/1994 | Alt . |
| 5,354,317 | 10/1994 | Alt . |

OTHER PUBLICATIONS

Bacharach et al., "Activity–Based Pacing: Comparison of a Device Using an Accelerometer Versus a Piezoelectric Crystal"*PACE*, vol. 15, pp. 188–196, Feb. 1992.

Alt et al., "A New Mechanical Sensor for Detecting Body Activity and Posture, Suitable for Rate Responsive Pacing", *PACE*, vol. 11, pp. 1875–1881, Nov., 1988, Part II.

"Airbags Boom When IC Accelerometer Sees 50G", *Electronic Design*, Aug. 8, 1991.

"Monolithic Accelerometer with Signal Conditioning", Rev. O, published Jun. 1993 by Analog Devices, Inc.

*Primary Examiner*—William E. Kamm
*Assistant Examiner*—Scott M. Getzow
*Attorney, Agent, or Firm*—Reed A. Duthler; Harold R. Patton

[57] ABSTRACT

A method of and apparatus for determining the physical posture of a patient's body, having a superior-inferior body axis, an anterior-posterior body axis and a lateral-medial body axis, in relation to earth's gravitational field. A medical device having first, second and, optionally, third DC accelerometers having sensitive axes mounted orthogonally within an implantable housing is adapted to be implanted with the sensitive axes generally aligned with the patient's body axes. Each DC accelerometer generates DC accelerometer signals having characteristic magnitudes and polarities on alignment of the sensitive axis with, against or normal to earth's gravitational field and DC accelerometer signals of varying magnitudes and polarities when not so aligned. Body position may be determined through comparison of the magnitudes and polarities of the DC accelerometer signals with the characteristic magnitudes and polarities. A patient activity signal may also be determined from the frequency of body movements recurring over a time unit effecting magnitude changes in the DC accelerometer signals within a certain range of magnitude and frequency. The activity and body position signals may be stored and/or used to monitor and effect the delivery of a therapy to the patient, e.g. by controlling the pacing rate of a rate responsive pacemaker.

29 Claims, 15 Drawing Sheets

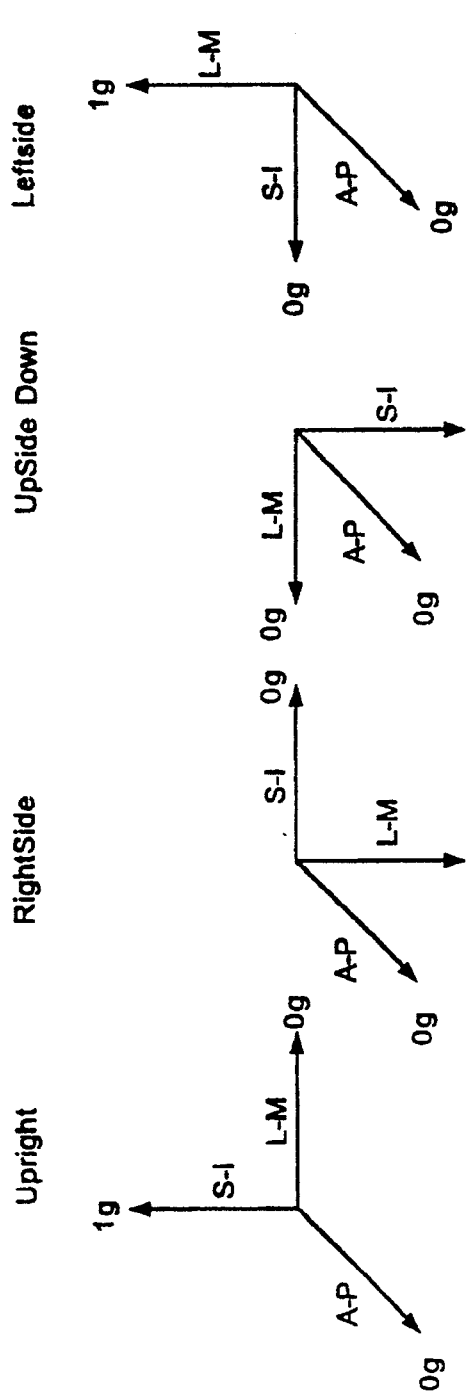
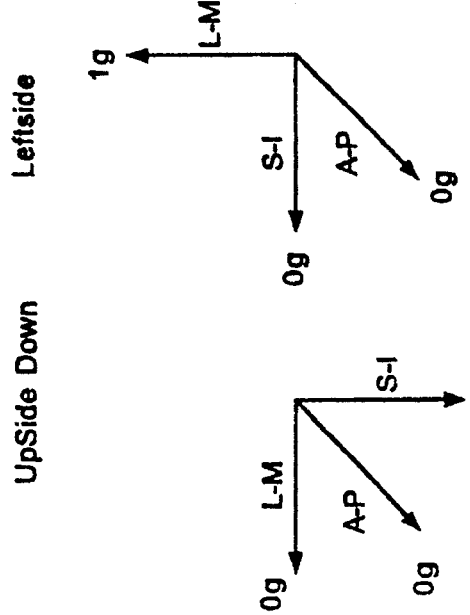
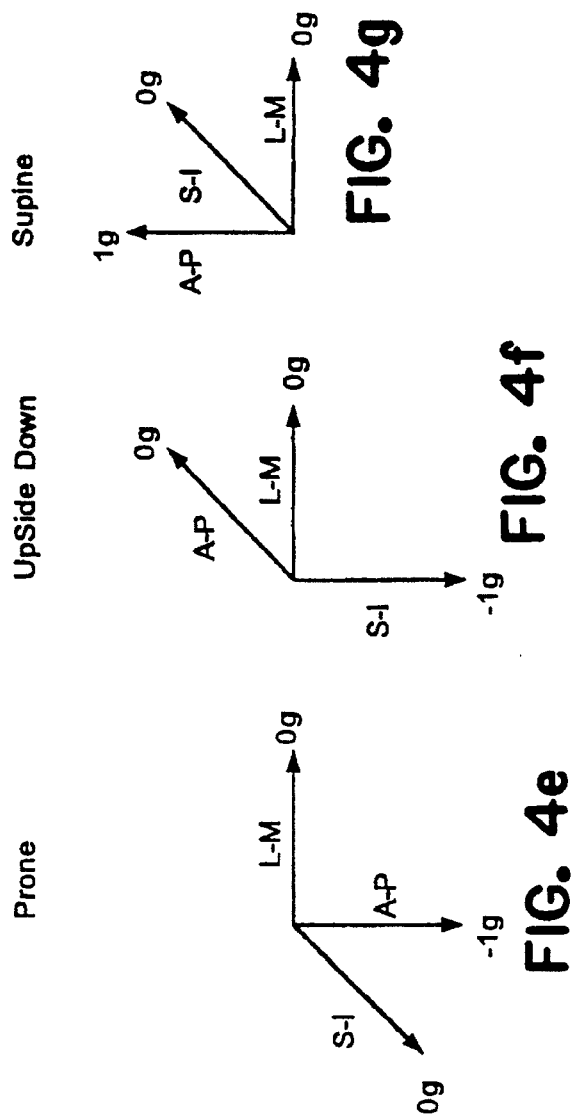
FIG. 4a  FIG. 4b  FIG. 4c  FIG. 4d  FIG. 4e  FIG. 4f  FIG. 4g

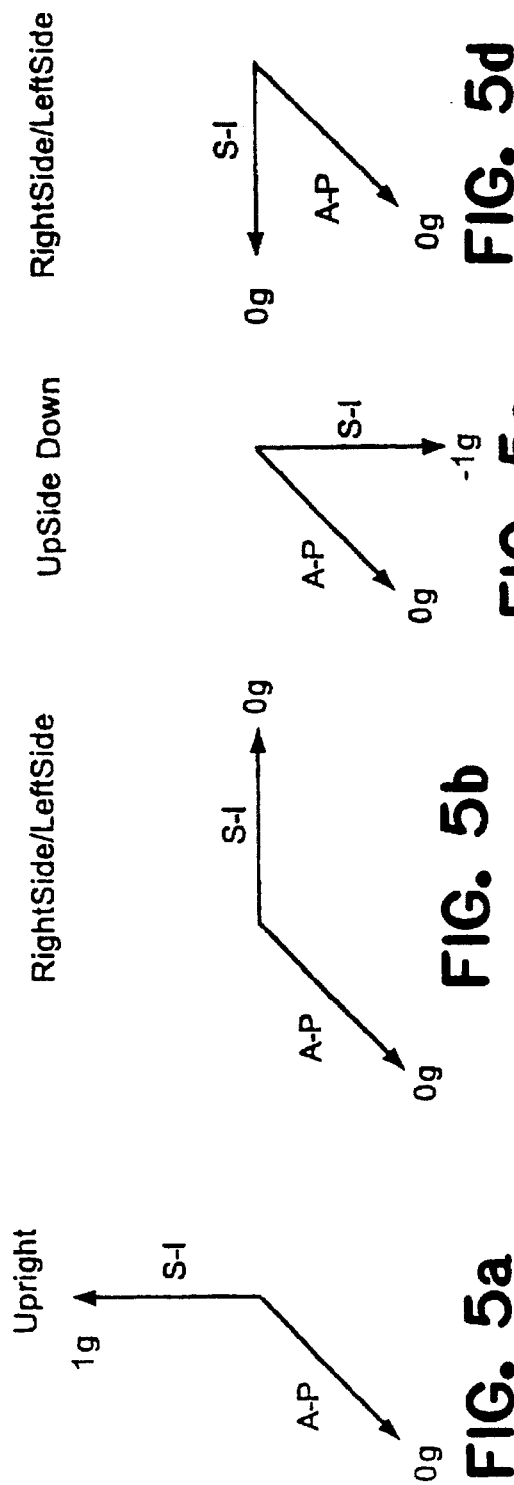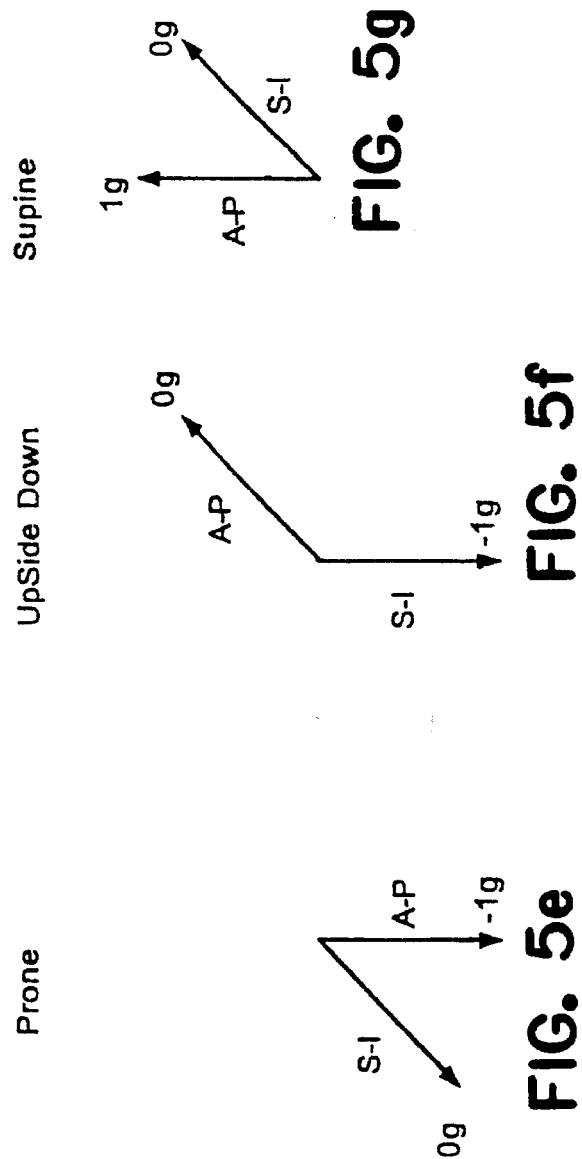

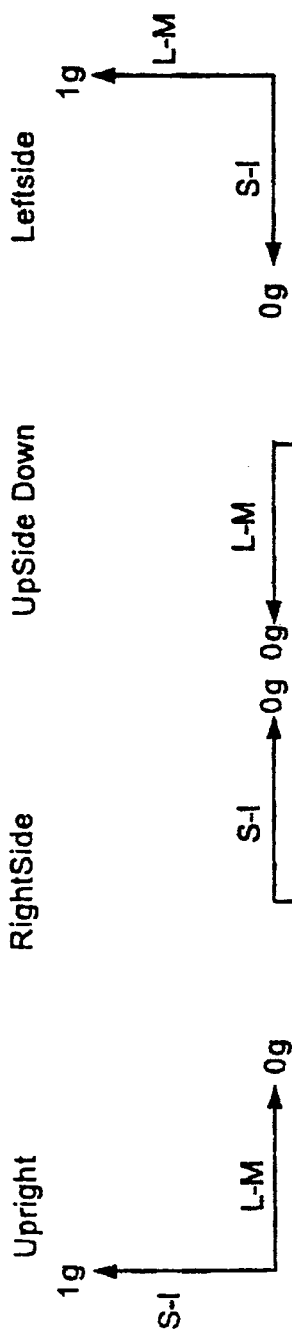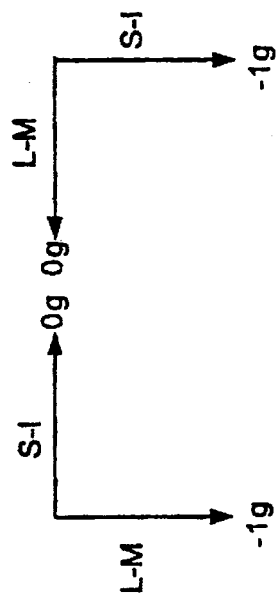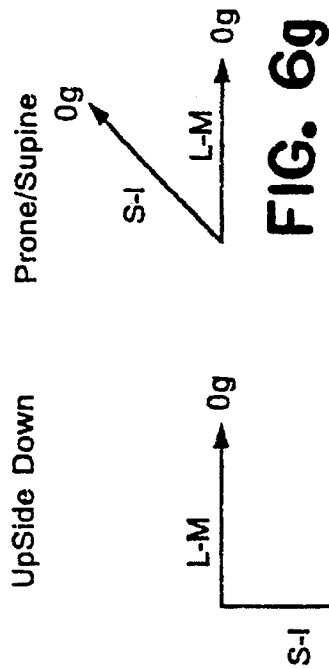

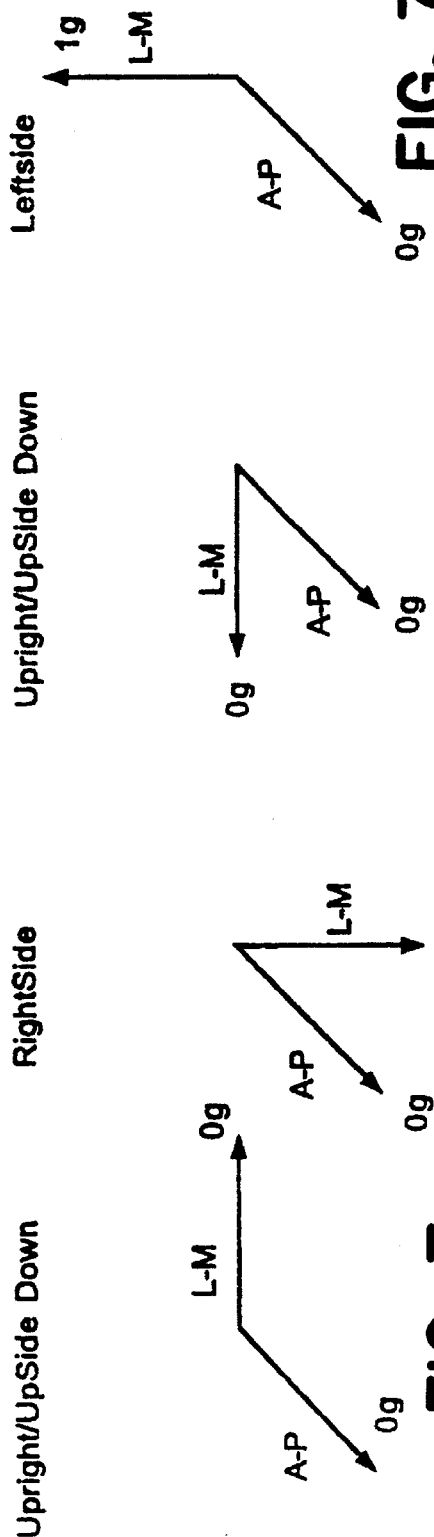
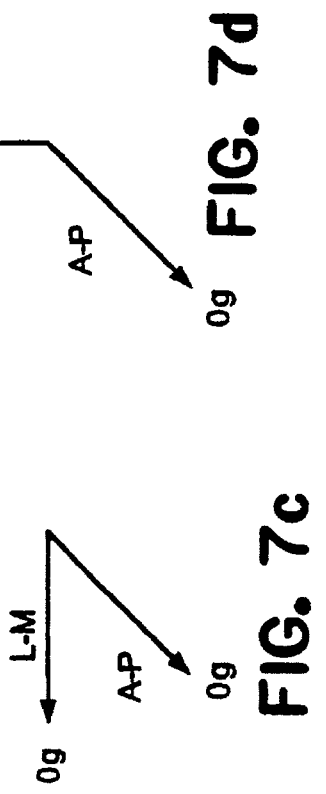
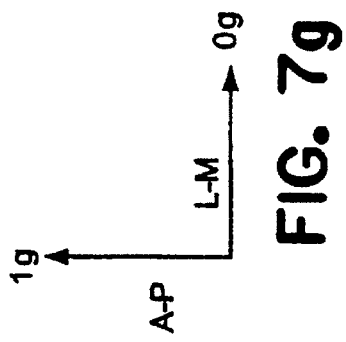
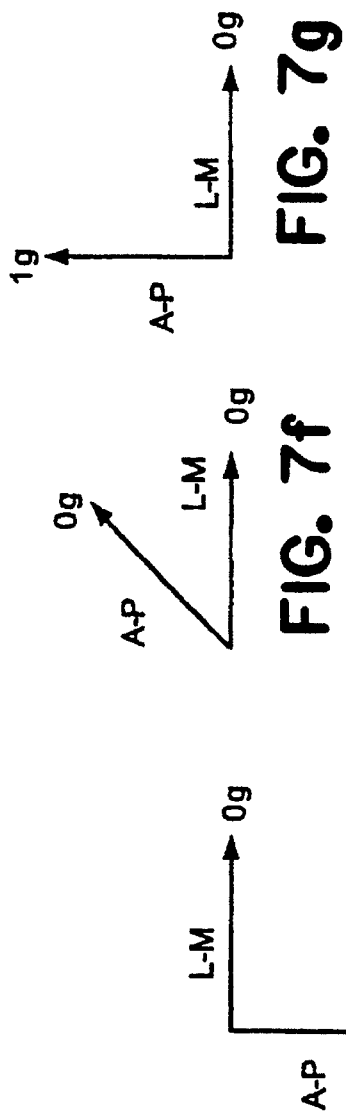

MEDICAL SERVICE EMPLOYING MULTIPLE DC ACCELEROMETERS FOR PATIENT ACTIVITY AND POSTURE SENSING AND METHOD

REFERENCE TO RELATED APPLICATION

Reference is made to commonly assigned co-pending U.S. patent application Doceket No. P-3270 entitled RATE RESPONSIVE CARDIAC PACEMAKER FOR DISCRIMINATING STAIR CLIMBING FROM OTHER ACTIVITIES filed on even date herewith.

BACKGROUND OF THE INVENTION

1. Field of the Invention

The present invention relates to the use of an array of DC accelerometers for detection of patient posture and activity level for medical monitoring and/or the delivery of therapies, including cardiac pacing.

2. Description of the Prior Art

In the field of medical device technology, patient monitoring of physiologic parameters e.g. heart rate, temperature, blood pressure and gases and the like are well known. In addition, the delivery of various therapies including drugs and electrical stimulation by implanted or invasive medical devices is well known. Factors that may be appropriately taken into account during monitoring or delivery of therapies include patient position or posture and activity level. Both may have an effect on the other parameters monitored and in the decision process for setting an appropriate therapy. Particularly in the field of cardiac pacing, patient activity level can be correlated to the need for cardiac output.

Rate responsive pacing has been widely adopted for adjusting pacing rate to the physiologic needs of the patient in relatively recent years. Early single chamber patient in relatively recent years. Early single chamber cardiac pacemakers provided a fixed rate stimulation pulse generator that could be reset, on demand, by sensed atrial or ventricular contractions recurring at a rate above the fixed rate. Later, dual chamber demand pacemakers became available for implantation in patients having an intact atrial sinus rate but no AV conduction, so that ventricular pacing could be synchronized with the atrial sinus rate, and backup fixed rate ventricular pacing could be provided on failure to sense atrial depolarizations. In addition, rate programmable pacemakers became available wherein the base pacing rate could be selected by a physician to provide a compromise fixed rate that did not interfere with patient rest and provided adequate cardiac output at moderate levels of exercise.

Such fixed rate pacing, particularly for patients not having an adequate atrial sinus rate to allow synchronous pacing, left most patients without the ability to exercise, lift objects or even walk up stairs without suffering loss of breath due to insufficient cardiac output. However, the introduction of the Medtronic® Activitrax® pacemaker provided patients with the a pulse generator having a rate responsive capability dependent on the level of patient activity. A piezoelectric crystal bonded to the interior of the implantable pulse generator can or case is employed in that pacemaker and successor models to provide a pulse output signal related to the pressure wave generated by a patient's footfall and conducted through the body to the crystal. Thus, low frequency activity signals recurring at the patient's rate of walking or running could be sensed and processed to derive a pacing rate appropriate to the level of activity. The activity sensor and its operation is described in commonly assigned U.S. Pat. No. 4,428,378 to Anderson.

Since the introduction of the Activitrax® pacemaker, a great many rate responsive pacemakers employing a wide variety of activity sensors and other physiologic sensors have been proposed and marketed. A comprehensive listing of such rate responsive pacemakers, sensors and sensed physiologic parameters is set forth in commonly assigned U.S. Pat. No. 5,226,413 to Bennett et al., incorporated herein by reference. However, the activity sensor of the type employed in the Activitrax® pacemaker continues to be used in successor single and dual chamber, rate responsive pacemaker models and remains the most widely used physiologic sensor.

As mentioned above, this piezoelectric crystal sensor is responsive to pressure waves generated by patient footfalls striking the exterior of the pulse generator case. Activity sensor configurations employing integrated circuit, AC accelerometers on an IC chip inside the pacemaker are also being employed in the EXCEL"VR pacemaker sold by Cardiac Pacemakers, Inc., and in similar rate responsive pacemakers sold by other manufacturers. The AC accelerometer is formed of a silicon beam mass suspended on the IC that swings or moves in response to shock waves caused by body motion and provides an output signal having a magnitude dependent on the rate of movement.

Like the piezoelectric crystal sensor, there is no signal output from the AC accelerometer in the absence of body motion and related to body position or attitude. In other words, when a patient is at rest, neither activity sensor provides any indication as to whether the patient is upright and awake and resting or lying down and presumably sleeping or resting. A lower sleep pacing rate than the rest pacing rate while awake and upright may be desirable for a given patient. Other sensors for sensing physiologic parameters induced by high levels of exercise have been proposed to detect the physiologic changes accompanying exercise, rest and sleep to trigger appropriate rates. Particularly, to lower the pacing rate during sleep, the inclusion of a real time clock to establish a Circadian rhythm pacing rate have also been proposed. None of these proposed sensors or systems are capable of determining a patient's position or posture.

A mechanical sensor has been proposed in the article "A New Mechanical Sensor for Detecting Body Activity and Posture, Suitable for Rate Responsive Pacing" by Alt et al. (*PACE*, Vol. 11, pp. 1875–81, November, 1988, Part II) and in Alt U.S. Pat. No. 4,846,195 that involves use of a multi-contact, tilt switch. This switch employs a mercury ball within a container that is proposed to be fixed in the pulse generator case, so that if the pulse generator is implanted at a certain orientation, and stays in that orientation, certain contacts are closed by the mercury ball when the patient is upright and others are closed or none are closed when the patient is prostrate, i.e., either prone or supine. During movement of the body, the mercury ball is expected to jiggle randomly and the number of contacts made per unit of time may be used as a measure of the level of activity. Similar sensors have been proposed in U.S. Pat. Nos. 4,869,251, 5,010,893, 5,031,618 and 5,233,984.

In the commonly assigned '984 patent, a cubic shaped multi-axis position and activity sensor is employed in rate responsive pacing applications and in the detection of tachycardia base on the patient being supine and inactive. In the commonly assigned '618 patent, a single axis position sensor is employed that is employed to control the therapy delivered by a spinal cord stimulator. The sensors in both patents employ conductive liquids, including an electrolyte or elemental mercury.

The use of elemental mercury is generally not favored and would increase environmental problems related to disposal of the pulse generators after use. Long term contact contamination and bridging issues would also arise, particularly given the extremely small size of the switch for confinement within modern pulse generator cases. To date, no implants of pacemaker pulse generators using such a tilt switch have been reported.

More recently, the use of a solid state position sensor in the form of a DC accelerometer is proposed in Alt U.S. Pat. No. 5,354,317. The DC accelerometer is fabricated in hybrid semiconductor IC form as a polycrystalline silicon, square plate, suspended at its four corners above a well in a single silicon crystal substrate, and associated low pass filter circuits are formed on the same substrate. The suspended plate structure moves between stationary positions with respect to the well on the suspension arms in response to earth gravity, depending on its orientation to the gravitational field. The plate also vibrates on the suspension arms similar to the AC accelerometer in response to acceleration movements of the patient's body.

In the pacemaker algorithms disclosed in the '317 patent, different base pacing rates are established depending on the static output of the position sensor that indicate the position of the patient, namely the upright, supine and prone positions, and separate base pacing rates can be set. Rate changes from the base pacing rates dependent on the exercise level of the patient in each position are suggested. Also, when changes in patient position are detected in the absence of physical exercise, the base pacing rate change is smoothed between the old and new rate to avoid a sudden step change.

The rate responsive pacemaker disclosed in the '317 patent offers some discrimination of patient position, but cannot distinguish among various patient positions where the suspended plate structure is aligned at the same angle to earth's gravitational field. The plane of the movable plate is at a fixed angle, e.g. coplanar, to a plane of the pulse generator case. Once the pulse generator is implanted in a patient, the movable plate plane may be aligned generally in parallel with the gravitational field and not detect the gravitational force (i.e., producing a zero amplitude output signal correlated to 0 g). The output of the so-aligned DC accelerometer would be the same whether a patient is standing, sitting or lying on either side, since the plate plane would remain in the same general parallel relationship to the gravitational field in all three positions. However, the pacing rates appropriate in standing, sitting or lying on a side are different when the patient is still.

The signal processing of the output signal from the single DC accelerometer of the '317 patent includes signal level calibration for each individual patient to account for differences in the angle of orientation of the DC accelerometer plate resulting from the implantation angle of the pulse generator case in the patient's body. However, this calibration is not suggested in order to distinguish body positions having a more or less common angular relation of the movable plate to the gravitational field.

Despite the weaknesses reported with respect to the piezoelectric sensors and solid state accelerometers, they remain favored over the other physiologic sensors that have been proposed or are in clinical use due to their relative simplicity, reliability, predictability, size, and low cost.

Problems to be Solved by the Invention

In view of the demonstrated advantages of the piezoelectric and AC accelerometer type activity sensors, it would be desirable to employ solid state sensors responsive to patient activity in a similar manner that would also distinguish between a wide variety of patient body positions for patient monitoring or in order to provide an appropriate therapy to a patient. Particularly, in a multi-programmable, rate responsive pacemaker, such a solid state sensor is desired to derive both patient activity signals and body position signals to set an appropriate pacing rate providing adequate cardiac output in each position and activity level.

SUMMARY OF THE INVENTION

In view of the above, it is an object of the present invention to provide a multi-axis, solid state position and activity sensor operable along at least two orthogonal axes to distinguish the posture or positional attitude of the patient at rest and at levels of exercise.

It is a further an object of the present invention to employ such a sensor to record body position and activity signal levels derived from the output signals of such a sensor.

It is yet a further an object of the present invention to employ such a sensor to employ body position and activity signal levels derived from the output signals of such a sensor in controlling the delivery of a therapy to a patient, including the delivery of drugs or electrical stimulation to the patient.

In a specific context, it is an object of the present invention to provide a rate responsive pacemaker with pacing rate setting capabilities that respond to a multi-axis solid state sensor operable along at least two orthogonal axes to distinguish the posture or positional attitude of the patient at rest and at levels of exercise.

It is yet a further particular object of the present invention to provide such pacing rate setting capabilities to provide a higher pacing rate for a resting patient that is standing upright than is provided for the same patient either sitting or a lying down supine, prone or on either side.

These and other objects of the invention are realized in a method of and apparatus for determining the physical posture of a patient's body, having a superior-inferior body axis, an anterior-posterior body axis and a lateral-medial body axis, in relation to earth's gravitational field comprising the steps of and means for: implanting a multi-axis, solid state sensor, comprising first and second DC accelerometers having first and second sensitive axes, respectively, which respond to earth's gravitational field to provide first and second respective DC accelerometer signals of a magnitude and polarity dependent on the degree of alignment therewith, in the patient's body so that said first and second sensitive axes are generally aligned with a respective first and second one of said superior-inferior, anterior-posterior or lateral-medial body axes; defining a first characteristic magnitude and polarity of said first and second DC accelerometer signals on alignment of the sensitive axes of said first and second DC accelerometers with earth's gravitational field, a second characteristic magnitude and polarity of said first and second DC accelerometer signals on alignment against earth's gravitational field, and a third characteristic magnitude and polarity of said first and second DC accelerometer signals on alignment normal to earth's gravitational field; deriving first and second DC accelerometer signals from said first and second DC accelerometers as the patient assumes various body positions moving said first or second sensitive axes generally into alignment with earth's gravitational field; and determining the body posture of the patient through comparison of the magnitudes and polarities of said derived first and second DC accelerometer signals with the magnitudes and polarities of said first, second and third characteristic magnitudes and polarities.

In accordance with the preferred embodiments of the invention, the stored posture and activity levels may retained in a monitor and/or be employed to control the delivery of a variety of therapies, including pacing, cardioversion/ defibrillation, other body stimulation therapies, and drug delivery therapies.

In the context of a pacemaker, the method and apparatus of the invention for pacing a patient's heart at a pacing rate dependent on patient activity and the physical posture of a patient's body, having a superior-inferior body axis, an anterior-posterior body axis and a lateral-medial body axis, in relation to earth's gravitational field, comprising the steps of and means for: measuring the constant acceleration of gravity on the patient's body in at least two of the superior-inferior, anterior-posterior, and lateral-medial body axes with first and second solid state DC accelerometer means aligned thereto for providing first and second DC accelerometer signals therefrom having a characteristic magnitude and polarity on alignment with earth's gravitational field and varying magnitude and polarity depending on the degree of mis-alignment of said first and second solid state DC accelerometer means with earth's gravitational field; determining a body position signal related to the posture of the patient through comparison of the magnitudes and polarities of the first and second DC accelerometer signals with said characteristic magnitudes and polarities; determining a patient activity signal from the frequency of body movements recurring over a time unit; deriving a rate control signal from the body position and patient activity signals correlated to the physiologic demand on the patient's heart in the determined body posture and level of activity; defining physiologic escape intervals as a function of the rate control signal to establish a physiologic pacing rate; generating pacing pulses at the physiologic pacing rate; and applying the pacing pulses to a chamber of a patient's heart.

Preferably, the posture of the patient is determined through the use of two or more solid state, DC accelerometers mounted in mutual orthogonal relationship within the pacemaker pulse generator case to derive two or more sets of signals dependent on the effect of gravity on the accelerometers which can be compared to derive the posture of the patient while standing, sitting, or prostrate in a variety of positions. With three DC accelerometers mounted orthogonally, the patient's body posture at rest may be derived and employed to set physiologic resting pacing rates appropriate to the patient in each of the possible positions.

The orthogonally mounted, DC accelerometers are preferably mounted into an IC chip so that the three sensitive axes are aligned with the three positional axes of the pulse generator housing. The physician can implant and stabilize the pulse generator housing in the proper orientation to the patient's thorax to align the sensitive axes with the superior-inferior (S-I), anterior-posterior (A-P), and lateral-medial (L-M) body axes of the chest region. As a result, distinctive signal levels are developed by each DC accelerometer in each posture position due to the effect of gravity on the DC accelerometer sensitive axes, so that posture of the patient can be correlated to the combination of the signal values.

One or more of the DC accelerometers can also be used to derive the level of patient activity from the number of changes in signal levels exceeding a certain threshold occurring in a given sampling time period, as is conventional in use of the piezoelectric and AC accelerometer activity sensors described above.

Advantages of the Invention

The use of the mutually orthogonal DC accelerometers and signal processing circuits and/or algorithms to determine the posture of the patient eliminates the limitations of the single DC accelerometer and does not involve acceptance of unusual materials and technology in an implantable device. The mutually orthogonal DC accelerometers and associated circuits can be easily incorporated into a pacemaker pulse generator or other medical device at low cost. The ease of use, and the reproducibility and consistency of results attained will lead to acceptability within the medical community.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein:

FIGS. 4a–4g is a graphical depiction of the sensitive axis orientations and output signals of the three orthogonally mounted DC accelerometers in a pulse generator of FIG. 2, implanted with the orientation shown in FIG. 2, when the patient is in a variety of positions;

FIGS. 5a–5g, 6a–6g, and 7a–7g are graphical depictions of the sensitive axis orientations and output signals of three pairs of the three orthogonally mounted DC accelerometers in a pulse generator of FIG. 2, implanted with the orientation shown in FIG. 2, when the patient is in a variety of positions;

DETAILED DESCRIPTION OF THE PREFERRED EMBODIMENTS

The present invention is preferably implemented in multi-programmable DDDR pacemakers of types widely known in the prior art. As described above with respect to other medical devices, the invention may also be implemented in other medical devices for providing other therapies and/or for monitoring physiologic parameters in the various body positions the patient may assume.

Figure 1:
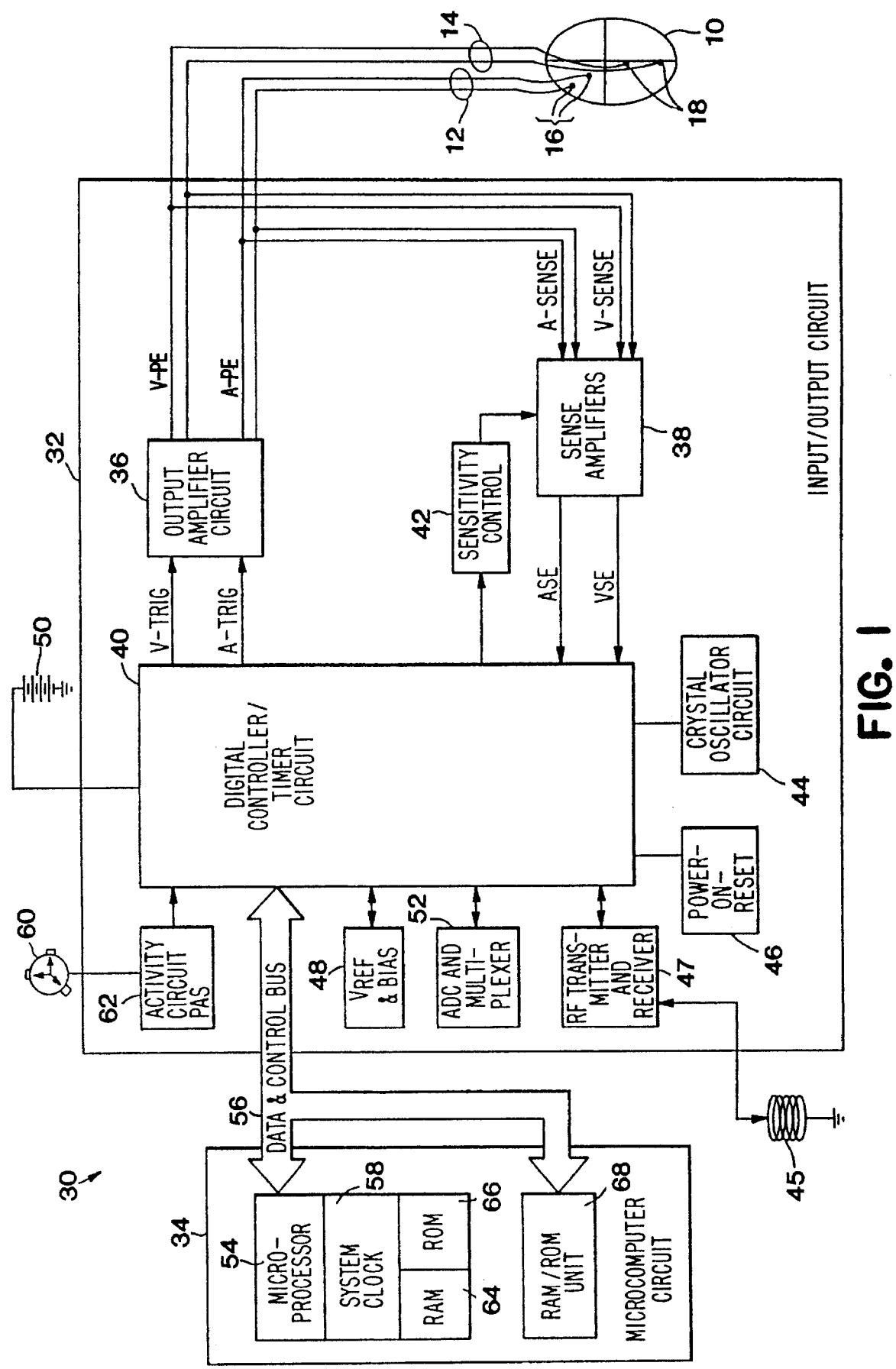
FIG. 1 is block level diagram of a DDDR pacemaker capable of implementing the mutually orthogonal DC accelerometers of the present invention as activity and patient posture sensors.

FIG. 1 is block level diagram of such a pacemaker implantable pulse generator or IPG 30 and lead set 12 and 14 which sets forth the structures required to incorporate the invention into a DDD/DDDR pacemaker. In the drawing, the patient's heart 10 has an atrial pacing lead 12 passed into the right atrium and a ventricular lead 14 passed into the right ventricle. The atrial lead 12 has an atrial electrode array 16 which couples the pulse generator 30 to the atrium. The ventricular lead 14 has a ventricular electrode array 18 for coupling the pulse generator 30 to the ventricle of the patient's heart 10. Atrial and ventricular leads 12 and 14 are depicted as bipolar leads coupled to a bipolar IPG 30, although unipolar leads could be employed with a suitable IPG.

The IPG circuit 30 of FIG. 1 is divided generally into a pacing circuit 32 coupled to a battery power supply 50, an activity sensor 60 of the type described below, a telemetry antenna 45 and a microcomputer circuit 34. The pacing circuit 32 includes the atrial and ventricular output amplifier circuit 36 and sense amplifiers 38 that are coupled to the atrial and ventricular leads 12 and 14, respectively, the digital controller/timer circuit 40 and other associated components described below. The output circuit 36 and sense amplifier circuit 38 may contain atrial and ventricular pulse generators and sense amplifiers corresponding to any of those presently employed in commercially marketed dual chamber cardiac pacemakers.

Sensed atrial depolarizations (A-SENSE) or P-waves that are confirmed by the atrial sense amplifier are communicated to the digital controller/timer circuit 40 on the ASE line. Similarly, ventricular depolarizations (V-SENSE) or R-waves that are confirmed by the ventricular sense amplifier are communicated to the digital controller/timer circuit 40 on VSE. The sensitivity control block 42 adjusts sensitivity of each sense amplifier in response to control signals provided by digital controller/timer 40 that are in turn stored in memory in microcontroller circuit 34.

In order to trigger generation of a ventricular pacing or VPE pulse, digital controller/timer circuit 40 generates a trigger signal on the V-trig line. Similarly, in order to trigger an atrial pacing or APE pulse, digital controller/timer circuit 40 generates a trigger pulse on A-trig line.

Crystal oscillator circuit 44 provides the basic timing clock for the pacing circuit 30, while battery 50 provides power. Reference mode circuit 48 generates stable voltage reference and current levels for the analog circuits within the pacing circuit 30 from the battery voltage and current. Power-on-reset circuit 46 responds to initial connection of the circuit 30 to the battery 50 for defining an initial operating condition and also resets the operating condition in response to detection of a low battery energy condition. Analog to digital converter (ADC) and multiplexor circuit 52 digitizes analog signals and voltage to provide real time telemetry of ASE and VSE cardiac signals from sense amplifiers 38, for uplink transmission via RF transmitter and receiver circuit 47. Voltage reference and bias circuit 48, ADC and multiplexor 52, power-on-reset circuit 46 and crystal oscillator circuit 44 may correspond to any of those presently used in current marketed implantable cardiac pacemakers.

Data transmission to and from an external programmer (not shown) is accomplished by means of the telemetry antenna 45 and the associated RF transmitter and receiver 47, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. and U.S. Pat. No. 4,374,382 issued to Markowitz. Uplink telemetry capabilities will typically include the ability to transmit stored digital information as well as real time or stored EGMs of atrial and/or ventricular electrical activity (according to the teaching of the above-cited Wyborny patent), as well as transmission of Marker Channel pulses indicating the occurrence of sensed and paced depolarizations in the atrium and ventricle, as disclosed in the cited Markowitz patent.

Control of timing and other functions within the pacing circuit 30 is provided by digital controller/timer circuit 40 which includes a set of timers and associated logic circuits connected with the microcomputer 34. Microcomputer 34 controls the operational functions of digital controller/timer 40, specifying which timing intervals are employed, and controlling the duration of the various timing intervals, via data and control bus 56. Microcomputer 34 contains a microprocessor 54, associated system clock 58, and on-processor RAM and ROM chips 64 and 66, respectively. In addition, microcomputer circuit 34 includes a separate RAM/ROM chip 68 to provide additional memory capacity. Microprocessor 54 is interrupt driven, operating in a reduced power consumption mode normally, and awakened in response to defined interrupt events, which may include the A-trig, V-trig, ASE and VSE signals. The specific values of the intervals defined are controlled by the microcomputer circuit 54 by means of data and control bus 56 from programmed-in parameter values and operating modes.

If the IPG is programmed to a rate responsive mode, the patient's activity level is monitored periodically, and the a sensor derived pacing escape interval is adjusted proportionally. A timed interrupt, e.g., every two seconds, may be provided in order to allow the microprocessor 54 to analyze the output of the activity circuit (PAS) 62 and update the basic V-A escape interval employed in the pacing cycle. In the DDDR mode, the microprocessor 54, the V-A escape interval may be selected as the variable pacing rate establishing interval, but the A-V interval and the atrial and ventricular refractory periods may also vary with the V-A escape interval established in response to patient activity.

Preferably two separate lower rate V-A interval timer functions are provided. The first is set by the physician when the base pacing rate is selected. This V-A time interval starts from the occurrence of a VPE or VPE, and provided neither an ASE nor a VSE occurs during the V-A time interval, an APE is generated after the expiration of the V-A time interval. The duration of the second lower rate time interval is a function of the measured patient activity acquired by the activity sensor 21. Typically, the V-A time interval begins with a VSE or VPE and has a time duration reflecting patient activity. In this art, such structures are well known, and a variety of techniques can be used to implement the required timer functions.

Digital controller/timer circuit 40 starts and times out these and other intervals employed over a pacing cycle comprising a successive A-V and V-A interval in a manner well known in the art. Typically, digital controller/timer circuit 40 defines an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 40 also defines the atrial refractory period (ARP) during which atrial sensing is disabled or the ASE is ignored for the purpose of resetting the V-A escape interval. The ARP extends from the beginning of the A-V interval following either an ASE or an A-trig and until a predetermined time following sensing of a ventricular depolarization or triggering the delivery of a VPE pulse. A post-ventricular atrial refractory period (PVARP) is also defined following delivery of a VPE pulse. The durations of the ARP, PVARP and VRP may also be selected as a programmable parameter stored in the microcomputer 34. Digital controller/timer circuit 40 also controls the pulse widths of the APE and VPE pacing pulses and the sensitivity settings of the sense amplifiers 38 by means of sensitivity control 42. Digital controller timer/logic circuit 40 also times out an upper rate limit interval (URL) set by a value programmed into memory in microcomputer circuit 34. This timer is initiated by the occurrence of a VPE or VSE, and limits the upper rate at which ventricular stimuli are delivered to the heart. The lower pacing rate is established by a programmed-in V-A or A-A interval value stored in memory in microcomputer circuit 34.

The illustrated IPG block diagram of FIG. 1 is merely exemplary, and corresponds to the general functional organization of most multi-programmable microprocessor controlled DDD(R) cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 66 of the microcomputer circuit 34. However, the present invention may also be usefully practiced by means of a full custom integrated circuit, for example, a circuit taking the form of a state machine as set forth in the above-cited Betzold et al. patent, in which a state counter serves to control an arithmetic logic unit to perform calculations according to a prescribed sequence of counter controlled steps. As such, the present invention should not be understood to be limited to a pacemaker having an architecture as illustrated in FIG. 1.

Figure 2:
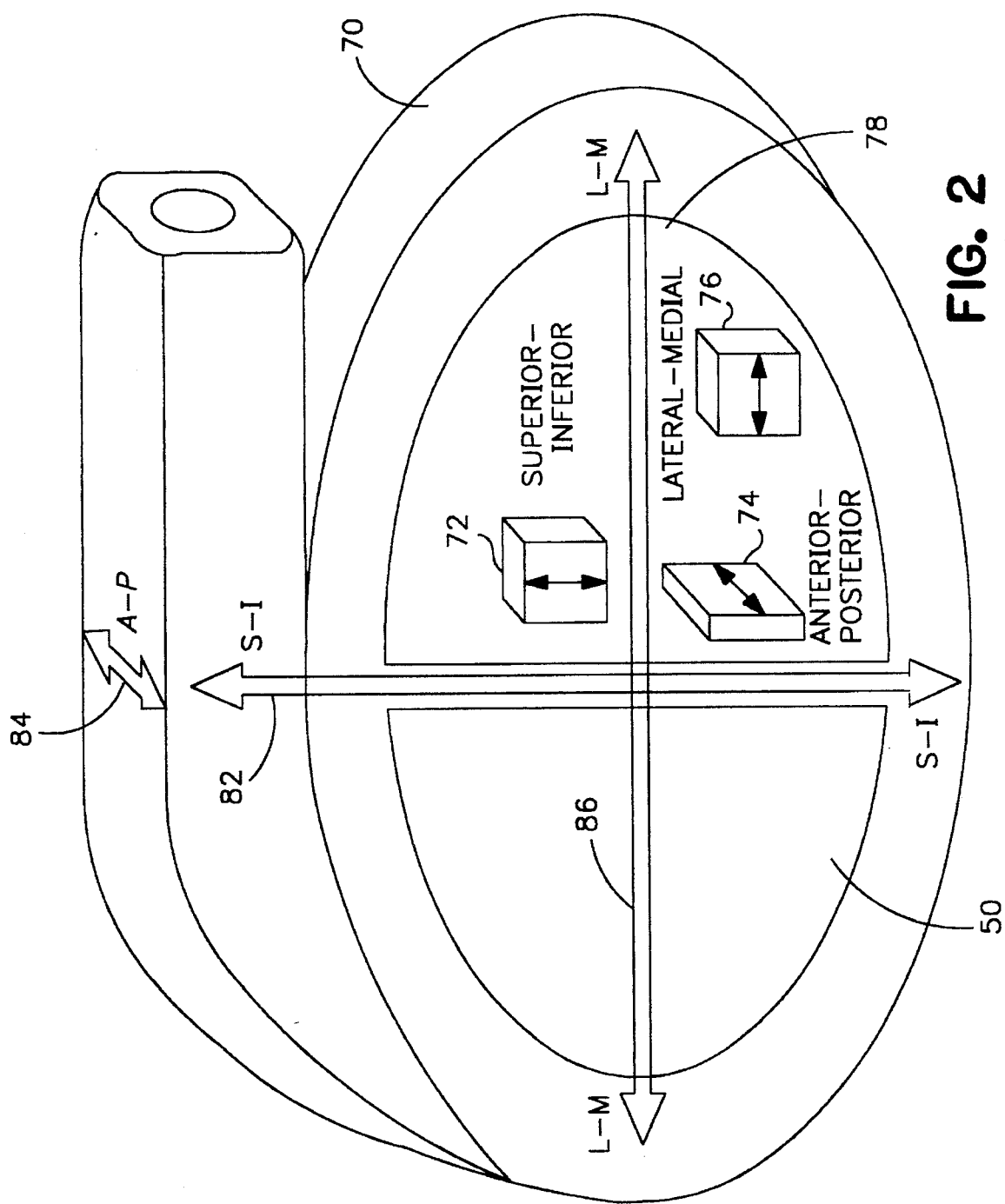
FIG. 2 is a schematic illustration of the orientations of the S-I, L-M, and A-P sensitive axes of three DC accelerometers mounted orthogonally with respect to a hybrid circuit substrate mounted within the housing for the pulse generator of FIG. 1 related to the markings on the housing for orienting the pulse generator with the patient body axes.
Figure 3:
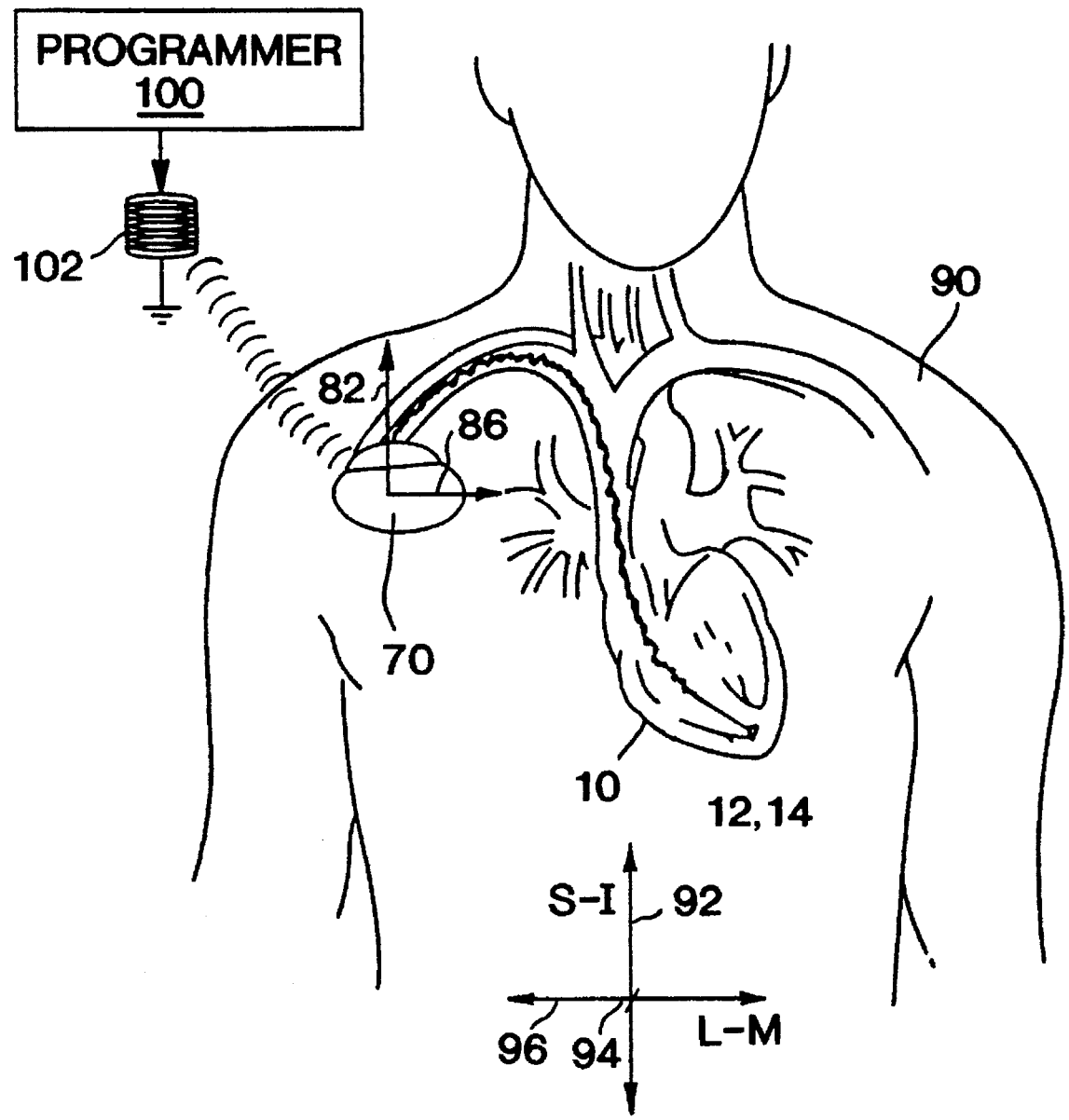
FIG. 3 is an illustration of the implantation of the pulse generator of FIG. 2 in a patient's body in substantial alignment with the S-I, L-M and A-P body axes.

Turning to FIGS. 2 and 3, they depict the pulse generator 30 within a housing 70 as it is intended to be implanted in a patient's body 90 with a lead or leads 12, 14 extending into the patient's heart 10. FIG. 2 is a schematic illustration of the solid state, S-I DC accelerometer 72, A-P DC accelerometer 74, and L-M DC accelerometer 76 mounted on the pulse generator hybrid circuit substrate 78 so that their sensitive axes are orthogonally directed to one another and are aligned with S-I, A-P and L-M positional axes 82, 84, and 86 marked on the exterior of the housing 70.

FIG. 3 schematically illustrates the implantation of the pulse generator case 70 so that the S-I, A-P and L-M positional axes 82, 84, 86, are aligned as closely as possible with the patient's S-I, A-P and L-M body axes 92, 94, 96, respectively. In each case, the A-P axis is directly into the plane of FIG. 3. An external programmer 100 of the type described above communicates with the implanted pulse generator 30 through conventional two-way RF telemetry employing the antenna 102. For example, the programmer described in the above-incorporated '413 patent may be employed in a patient work up to determine the degree to which the S-I, A-P and L-M sensitive axes of the respective DC accelerometers 72, 74, 76 are aligned with the patient's S-I, A-P and L-M body axes 92, 94, 96, respectively. This may be accomplished by having the patient assume the resting positions to accumulate average output signals of each of the DC accelerometers 72, 74, 76 in pulse generator memory and then command telemetry out of the signals using the programmer 100. Then, the deviations in the output signal amplitudes from a standard amplitude expected from alignment of the sensitive axis with earth's gravitational field may be employed to normalize the output signals.

Each of the DC accelerometers 72, 74, 76 is preferably a surface micromachined integrated circuit with signal conditioning, e.g. the Model ADXL 50 accelerometer sold by Analog Devices, Inc., Norwood Mass. and described in detail in the article "Airbags Boom When IC Accelerometer Sees 50G", in the Aug. 8, 1991, issue of *Electronic Design*, and in "Monolithic Accelerometer with Signal Conditioning", Rev. O, published by Analog Devices, Inc., both incorporated herein by reference in their entirety. Employing surface micromachining, a set of movable capacitor plates are formed extending in a pattern from a shaped polysilicon proof mass suspended by tethers with respect to a further set of fixed polysilicon capacitor plates. The proof mass has a sensitive axis along which a force between 0 G and ±50 G effects physical movement of the proof mass and a change in measured capacitance between the fixed and movable plates. The measured capacitance is transformed by the on-chip signal conditioning circuits into a low voltage signal.

The proof mass of the ADXL 50 is coplanar with the IC chip plane it is tethered to for movement back and forth in positive and negative vector directions along a single sensitive axis. The planar orientation thus provides that the proof mass sensitive axis is along the length of the proof mass. For off the shelf use, the ADXL 50 IC chip is mounted in a TO-5 can with the positive vector direction of the sensitive axis aligned to a reference tab of the can. By using to the can tab, the positive or negative vector direction of the sensitive axis can be aligned with respect to some plane or angle of the system or circuit it is used in with respect to the constant vertical direction of gravitational force. The reference tabs for the three axes are schematically illustrated in activity sensor 60 of FIG. 1 and with respect to each of the DC accelerometers 72, 74 and 76 of FIG. 2. Of course, in actual custom fabrication within the pulse generator 30, the DC accelerometers would be formed or assembled on a single IC chip and the assembly could be enclosed in a single IC package mounted to hybrid substrate 78. The assembly of the hybrid substrate 78 within the pulse generator housing 70 is precisely controlled to establish the orientation.

The effect of 1 G of gravitational force applied directly along the sensitive axis of a stationary ADXL 50 accelerometer provides a characteristic output voltage signal level that is referenced or scaled as +1 for angular computation purposes. The effect of 1 G of gravitational force applied in precisely the opposite or negative direction to the sensitive axis provides a characteristic output voltage signal level that is referenced or scaled as −1. If the sensitive axis is oriented transversely to the direction of the gravitational force, a bias voltage level output signal should be present, and that voltage signal level is referenced or scaled as 0. The degree to which the sensitive axis is oriented away or tilted from the direction of the gravitational force can also be detected by the magnitude and polarity of the output voltage signal level deviating from the bias level scaled to 0 and below the output signal level values scaled to +1 and −1. The above-referenced publications provide instructions for scaling the voltage signal levels to the 0, +1 and −1 static level values. A microprocessor interface circuit with auto calibration of offset error and drift caused by temperature variation that may be employed in the activity circuit 62 of FIG. 1 is also described.

Other scales may be employed, depending on the signal polarities and ranges employed. The examples described below with reference to the data collected in testing and illustrated in FIG. 15 employ a scale where 0 G develops a 1.000 volt DC signal, +1 G develops a +1.400 volt DC signal and −1 G develops a +0.600 volt signal.

The effect of instantaneous or AC changes due to body motion acceleration can be measured by the voltage signal output level changes per unit time. As indicated in the above-incorporated publications, the ADXL 50 can discriminate instantaneous acceleration levels up to 50 Gs, which is well in excess of the sensitivity required to detect patient footfalls regardless of the intensity level that a patient could muster. The output signal levels may be scaled to a lower range, e.g. 0 to ±2–5 G through adjustment of the internal ADXL 50 buffer amplifier or custom fabrication.

Returning to FIG. 2, when the three DC accelerometers 72, 74 and 76 of the ADXL 50 type are incorporated into a pulse generator as depicted, the sensitive axis of S-I DC accelerometer 72 is intended to be aligned, when the pulse generator 30 is implanted, as close to vertical and the patient's S-I body axis 92 as possible. Thus, when standing upright and remaining still, the output signal level +1 should be realized or closely approached by the S-I DC accelerometer 72. At the same time, the output signal levels of the A-P and L-M DC accelerometers 74 and 76 should approach 0.

When the patient lies still on his/her back or stomach, the signal levels of the A-P DC accelerometer 74 should approach +1 or −1, respectively (if the pulse generator housing 70 is implanted with the A-P DC accelerometer positive vector pointed anteriorly), while the signal levels of the S-I and L-M DC accelerometers 72 and 76 should approach 0. In the same fashion, the patient lying on the right and left sides will orient the sensitive axis of the L-M DC accelerometer 76 with the gravitational force to develop either the +1 or −1 signal level while the signal levels of the S-I and A-P DC accelerometers 72 and 74 should approach 0.

Deviations from the absolute value signal levels +1, 0 and −1 of each DC accelerometer 72, 74 and 76 can be measured after implantation during a patient work up in these positions employing the external programmer 100. The deviations may be stored in RAM 64 as adjustment values to be used by the microprocessor in weighting or otherwise processing the actual scaled output signal levels of the three DC accelerometers 72, 74 and 76 periodically supplied to the microcomputer circuit 34 through the digital controller/timer circuit 40. Moreover, the actual implantation orientations of the positive axis vectors of A-P and L-M DC accelerometers 74 and 76 can also be determined by the polarity of the signals generated, and those orientations may be stored in the microcomputer memory and employed to change the polarity of the output signal levels of the three DC accelerometers 72, 74 and 76 as necessary. One manner of adjusting the sensitivity and accuracy of the body position discrimination is set forth below with respect to FIGS. 13 and 14.

The means and method for determining the physical posture of the patient operates through a comparison of the magnitudes and polarities of the first and second DC accelerometer signals or first second and third DC accelerometer signals depending on whether two or three DC accelerometers 72, 74, 76 are used. The above description provides a framework for developing a set of equations for deriving the patient's physical posture or position while at rest and while moving through a comparison of the magnitudes and polarities of the first, second and third DC accelerometer signals generated by the three DC accelerometers 72, 74 and 76.

FIGS. 4a–4g shows the sensitive axes of the three DC accelerometers 72, 74 and 76 in a pulse generator implanted with the orientation shown in FIGS. 2 and 3 when the patient's body is in a variety of positions generally orienting one of the patient's S-I, A-P and L-M body axes 92, 94, 96, with earth's gravitational field. FIGS. 5a–7g show the sensitive axes of selected pairs of the three DC accelerometers 72, 74 and 76 used in a pulse generator 30 in a first variation of the preferred embodiment having only two of the three DC accelerometers depicted in FIG. 2, when the patient's body is in a variety of positions generally orienting one of the patient's S-I, A-P and L-M body axes 92, 94, 96, with earth's gravitational field.

In each illustration of FIGS. 4a–7g, the direction of gravitational force is vertical to an imaginary plane at the juncture of the axes. Thus, for example, in FIG. 4a, in the patient's upright position, the S-I DC accelerometer 72 sensitive axis and positive direction vector is up outputting a +1 scaled signal level. The sensitive axes of the A-P and L-M DC accelerometers 74 and 76 are normal to the gravitational force resulting in scaled 0 signal levels. In the supine right (FIG. 4b) and left (FIG. 4d) side positions, the L-M DC accelerometer scaled output level is −1 and +1, respectively, while the other two DC accelerometer signal levels are scaled at 0. All of the positions of FIGS. 4a–g are similarly distinguishable by the comparison of the scaled output signal levels.

Turning to FIGS. 5a–7g, similar position discrimination may be achieved with less resolution using only two DC accelerometers. It is not possible with two DC accelerometers to distinguish all of the illustrations of FIGS. 4a–g.

The microcomputer circuit 34 may be programmed to compare the mean or average scaled signal level values of either the two or three DC accelerometers to a set of stored values or windows for each position to make the determination of the patient's current position. Then, dependent on the position and the current activity level, the escape interval providing the base pacing rate may be derived that is appropriate. In the DDDR pacemaker of FIG. 1, the A-A or V-A base escape interval may be adjusted between a lower and an upper rate escape interval.

Figure 8:
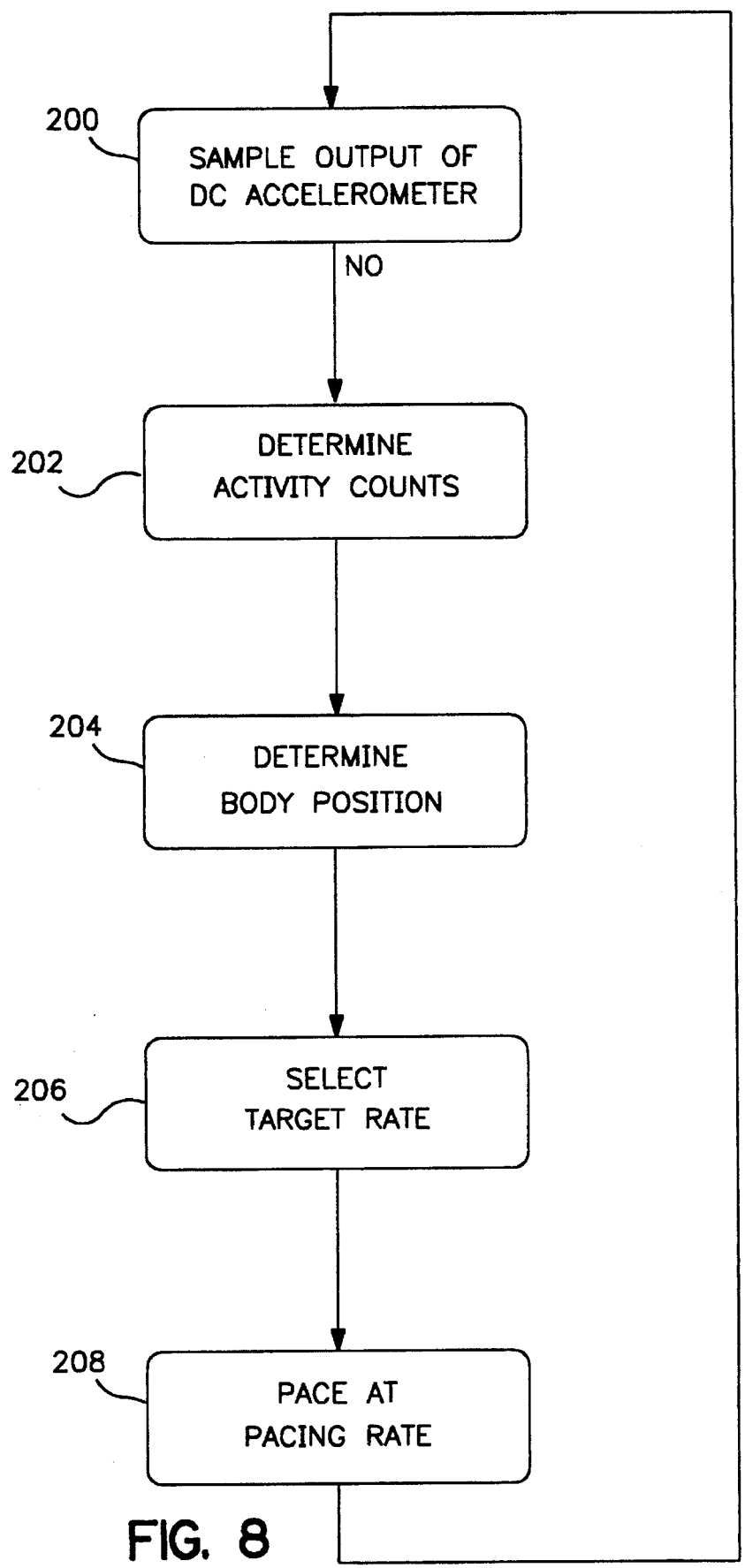
FIG. 8 is a rate response overview flowchart of the algorithm incorporated into the pacemaker of FIG. 1 for deriving a physiologic pacing rate from the output signals of two or three DC accelerometers of FIG. 2.

FIG. 8 depicts an overall flowchart for accomplishing an operating routine in the pulse generator 30 of FIG. 1 from the output signals of two or all three of the three DC accelerometers of FIG. 2. In step 200, the output signals of the two or three DC accelerometers are sampled in a multiplex manner to first determine the degree of activity of the patient in step 202. The current exercise activity level of the patient may be derived from a count of the activity events. An activity event is detected when an output signal of one or more of the DC accelerometers 72, 74 and/or 76 (if all three are present) in the frequency range of 1–10 Hz is detected that exceeds a positive or negative scale threshold. The Activity Count is determined in a conventional process of filtering the sampled output signal in the 1–10 Hz frequency range, amplifying the filtered signal, comparing the amplified signal to a threshold level, and counting the threshold exceeding signals over a unit time period, e.g. two seconds.

For example, the patient's footfalls cause shock waves to be transmitted through the body that drive the A-P DC accelerometer 74 to develop alternating output signals within the specified frequency range for walking or running. Those sampled values exceeding the activity threshold level are characterized as activity events. The activity events are counted in microprocessor 54 over a running time period, e.g. 2 seconds, to derive the Activity Count. Arm and leg motion accompanying prone exercises, e.g. swimming, may also generate activity events.

The Activity Count may be employed to trigger the determination of the body position in step 204 and to select a Target Rate appropriate to the estimated level of exercise in the determined body position in step 206. The Target Rate for pacing the patient's heart is proportional to the Activity Count and varies between the programmed pacing Lower and Upper Rates in a manner well known in the art. In accordance with the present invention, the determined body position may be employed to direct the selection of a Target Rate from sets of Target Rates correlated to Activity Counts for each body position. For example, look-up tables in ROM memory 66 or RAM/ROM unit 68 may be programmed with the sets of Target Rates. Alternatively, a single Target Rate may be correlated to or derived from the Activity Count and then mathematically adjusted upward or downward as a function of the determined body position.

However finally derived, the Target Rate is employed as a pacing rate control signal in step 208. The Target Rate may be subjected to further modification in step 208 through rate smoothing to avoid abrupt rate changes from a prevailing rate, or the like, in a manner well known in the art.

Figure 9:
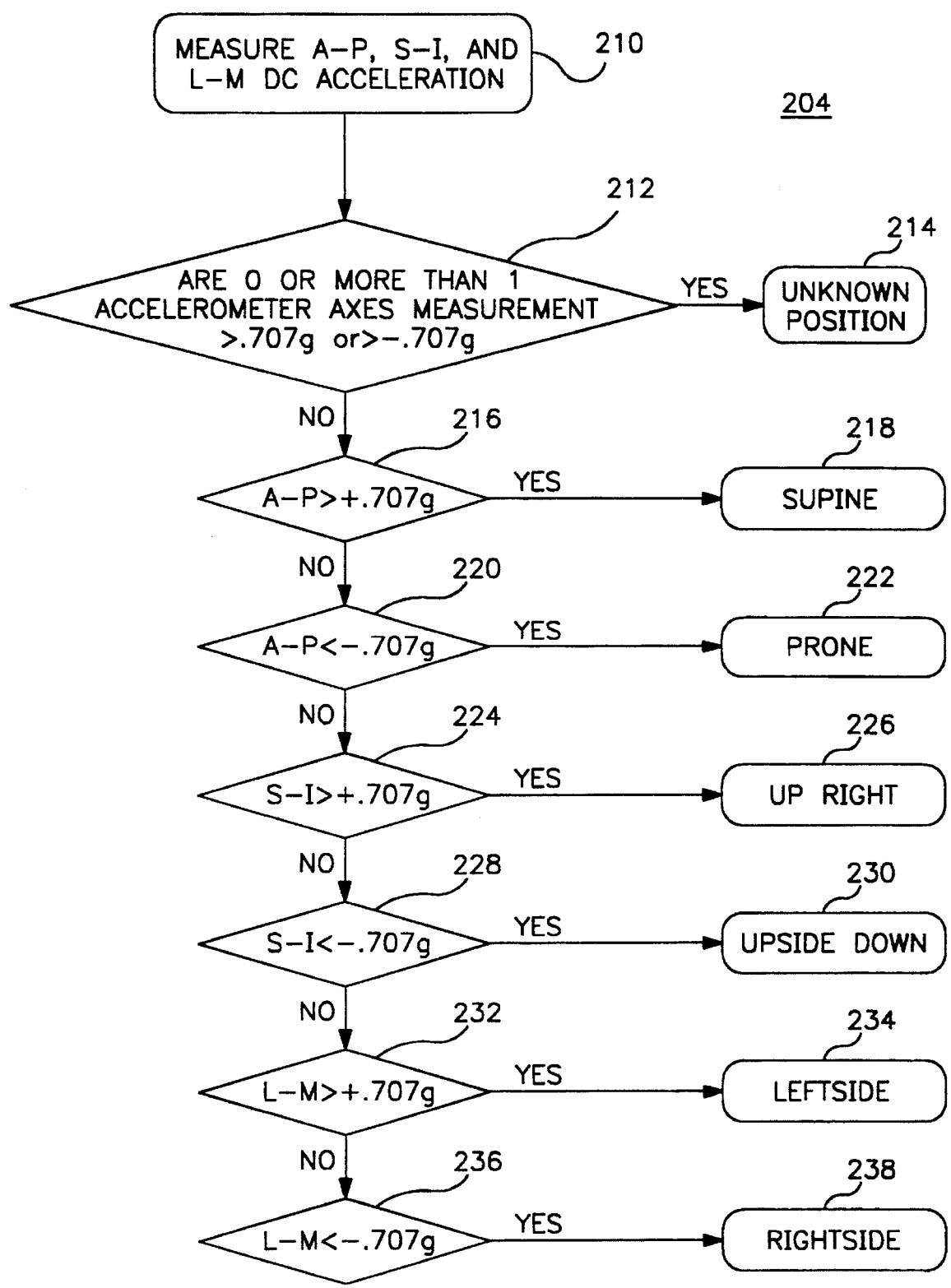
FIG. 9 is a flowchart of a first embodiment of the algorithm for determining body position from the DC components of the output signals of all three of the DC accelerometers of FIG. 2.

Turning to FIG. 9, it illustrates a first method of determining the body position or posture from the DC signal levels of the three DC accelerometers employed as step 204 of FIG. 8. In step 210, the DC acceleration samples from step 200 are averaged out over the sample period. DC signal levels generated by the force of gravity on each of the three accelerometers 72, 74, 76 depend on the orientation of the sensitive axes to the force of gravity as described above. In step 212, a default condition is tested. If no DC signal level or if two or more DC signal levels are greater than the threshold signal levels generated by +0.707 G or less than —0.707 G, then the position is not determinable for some reason. In this case, the Target Rate would be determined solely from the Activity Count in step 206 of FIG. 8.

The discrimination provided by this embodiment of step 204 (and the embodiments of FIGS. 10–12) is simplified by certain assumptions and the linear output response of the ADXL 50 accelerometers to the direction of earth's gravitational field. The orientation of any of the sensitive axes 72, 74, 76 at ±45° to the horizon effects a force of +0.707 G on the moving element. Similarly, the orientation of any of the sensitive axes 72, 74, 76 at –45° to the horizon effects a force of –0.707 G on the moving element. Thus, windows may be defined that border the ±45° tilt values to categorize the patient body position from the DC output signals of the two or three DC accelerometers.

Assuming that the conditions of step 212 are not met, then the DC signal levels generated by the A-P, S-I, and L-M DC accelerometers under the influence of the gravitational field are compared to threshold signal levels that would be generated by +0.707 G and –0.707 G in the particular order depicted in steps 216–238. When a stated comparison is satisfied, then the position is determined for use in step 206 of FIG. 8. For example, if none of the preceding conditions of steps 216, 220, 224 are satisfied, and the condition of step 228 (that the S-I DC signal level is less than the threshold for –0.707 G) is satisfied, then the body position is determined to be Upside Down in step 230, and an appropriate Target Rate related to the Activity Count is selected in block 206. The possible sensitive orientations depicted in FIG. 4 may be related to the conditions expressed in steps 216–238.

Figure 10:
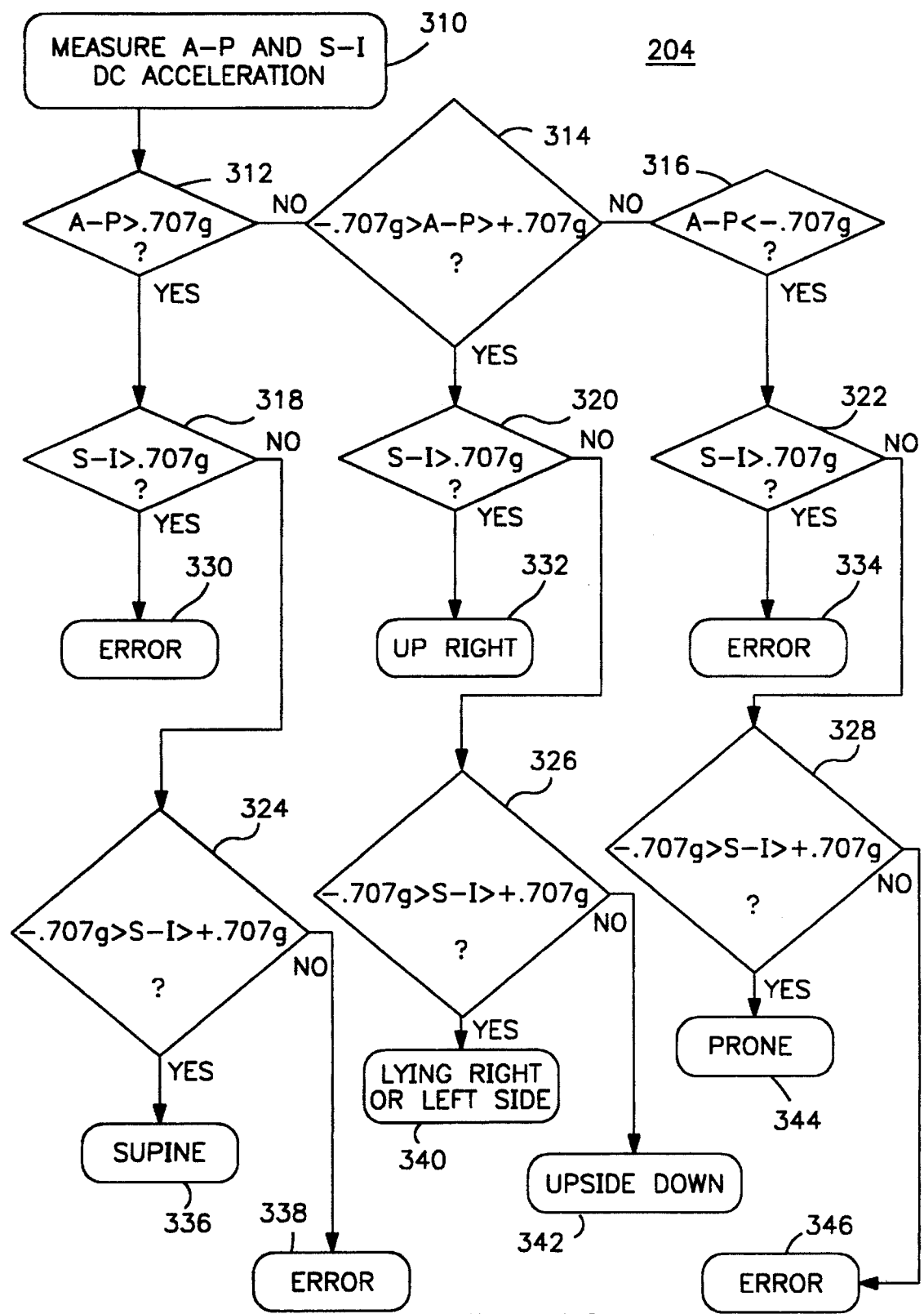
FIGS. 10–12 are flowcharts of a first embodiment of the algorithm for determining body position from the DC components of the output signals of two of the three DC accelerometers of FIG. 2.
Figure 11:
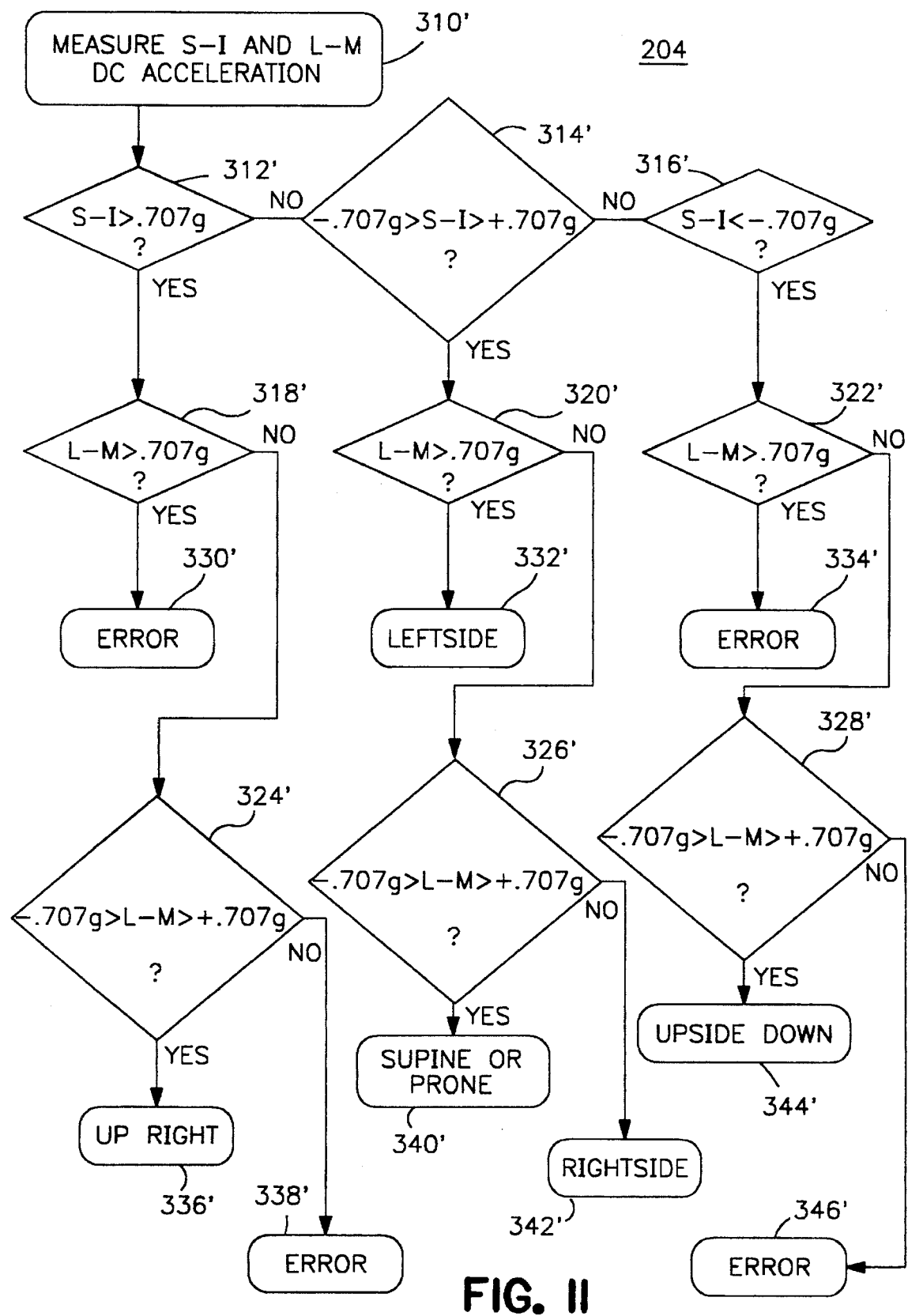
Figure 12:
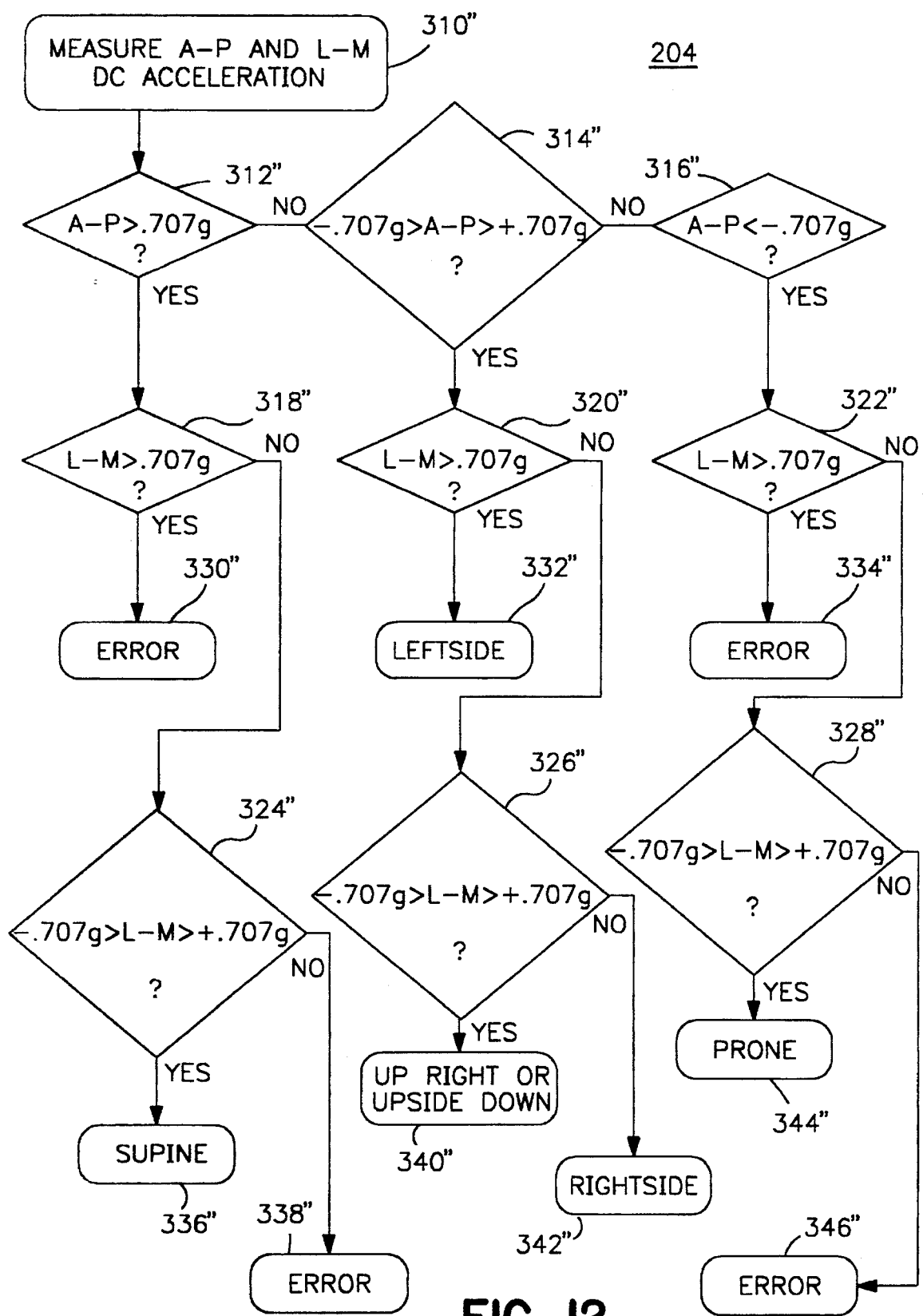

Turning to FIGS. 10–12, alternate steps 204 are depicted for the use of only two of the three DC accelerometers for the determination of a lesser number of determinable body positions. The pairs of DC accelerometers employed in FIGS. 10–12 correspond to those depicted in FIGS. 5–7. In each case, the DC signal levels of the two sensors are compared to the threshold signal levels that would be generated by +0.707 G and –0.707 G acting on the accelerometer. All three flowcharts are essentially the same in operation and differ only in the DC accelerometer signal output compared to the threshold signal levels and the resulting determination of position. As in FIG. 8, once a condition is satisfied, then the position or inability to confirm a position is declared, and the Target Rate is selected in step 206 of FIG. 8. In view of the similarity of the process for each selected pair, only FIG. 10 will be described in some detail.

In step 310, the DC acceleration samples of the DC signal of the A-P and S-I DC accelerometers from step 200 are averaged out over the sample period. In steps 312, 314 and 316, the A-P signal level is compared to the +0.707 G and/or –0.707 G threshold signal levels until one of the conditions is satisfied. Then, when one of the conditions of steps 312–316 is satisfied, the S-I signal level is compared to the 0.707 G threshold signal level in one of the steps 318, 320, or 322. If the S-I signal level is not greater than the 0.707 G threshold signal level, then the S-I signal level is compared to the +0.707 G and –0.707 G threshold signal level in one of the steps 324, 326, or 328. As a result of the successive steps of comparison, one of the body position determinations of steps 330–346 is declared, and an appropriate Target Rate related to the Activity Count is selected in block 206.

In FIG. 11, a similar process is followed in the comparison steps 312'–328' and the determination steps 330'–346'. Likewise, in FIG. 12, a similar process is followed in the comparison steps 312"–328" and the determination steps 330"–346". As can be seen, the use of two DC accelerometers results in indeterminate or error positions being declared for certain positions which may limit these embodiments to special applications. On the other hand, it may be unnecessary to distinguish between prone or supine, leftside or rightside, and upright or upside down in many applications.

Figure 13:
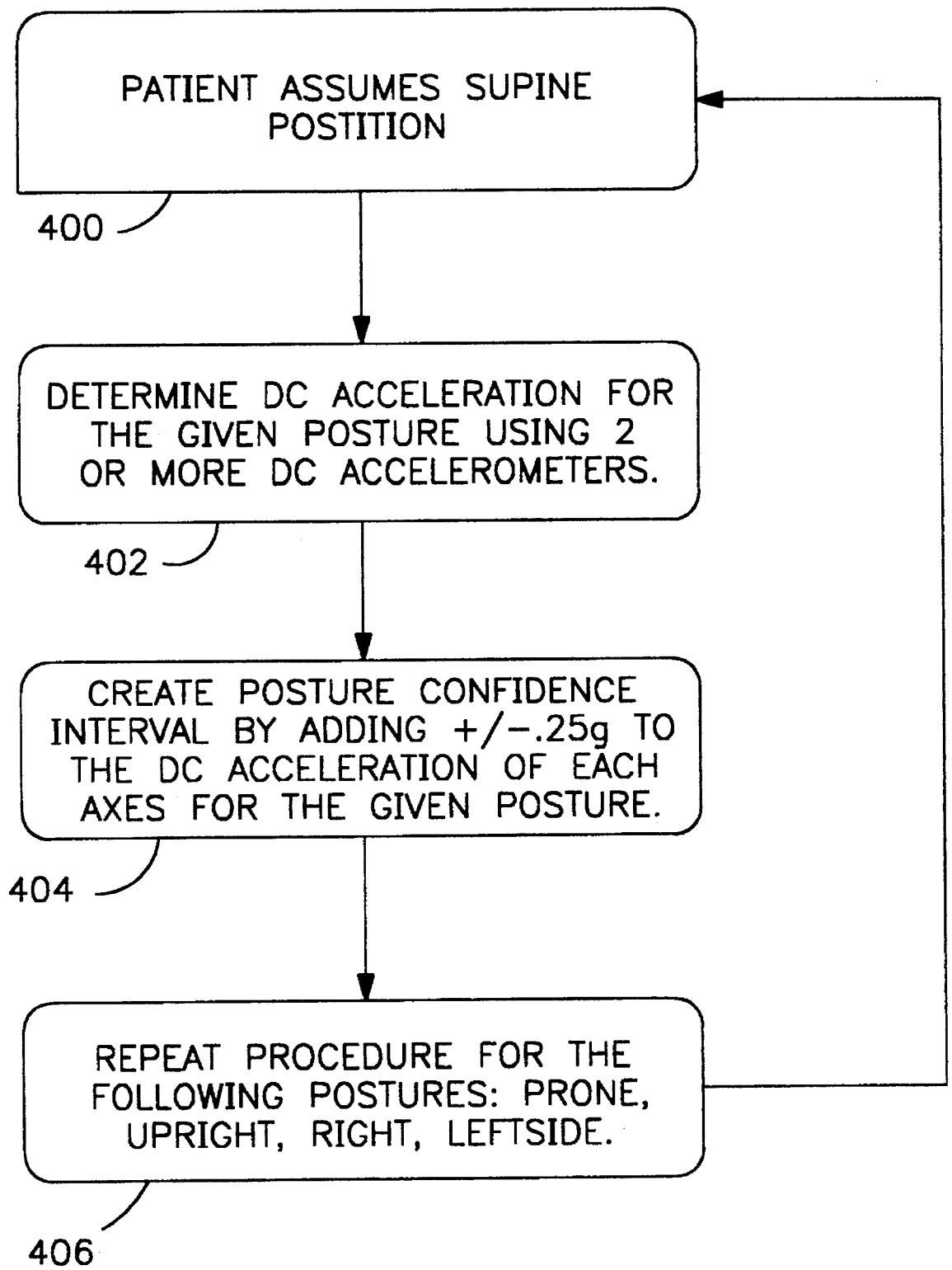
FIG. 13 is a flowchart of a patient workup for deriving a posture confidence interval from the DC components of the output signals of any selected two or all three of the DC accelerometers of FIG. 2.
Figure 14:
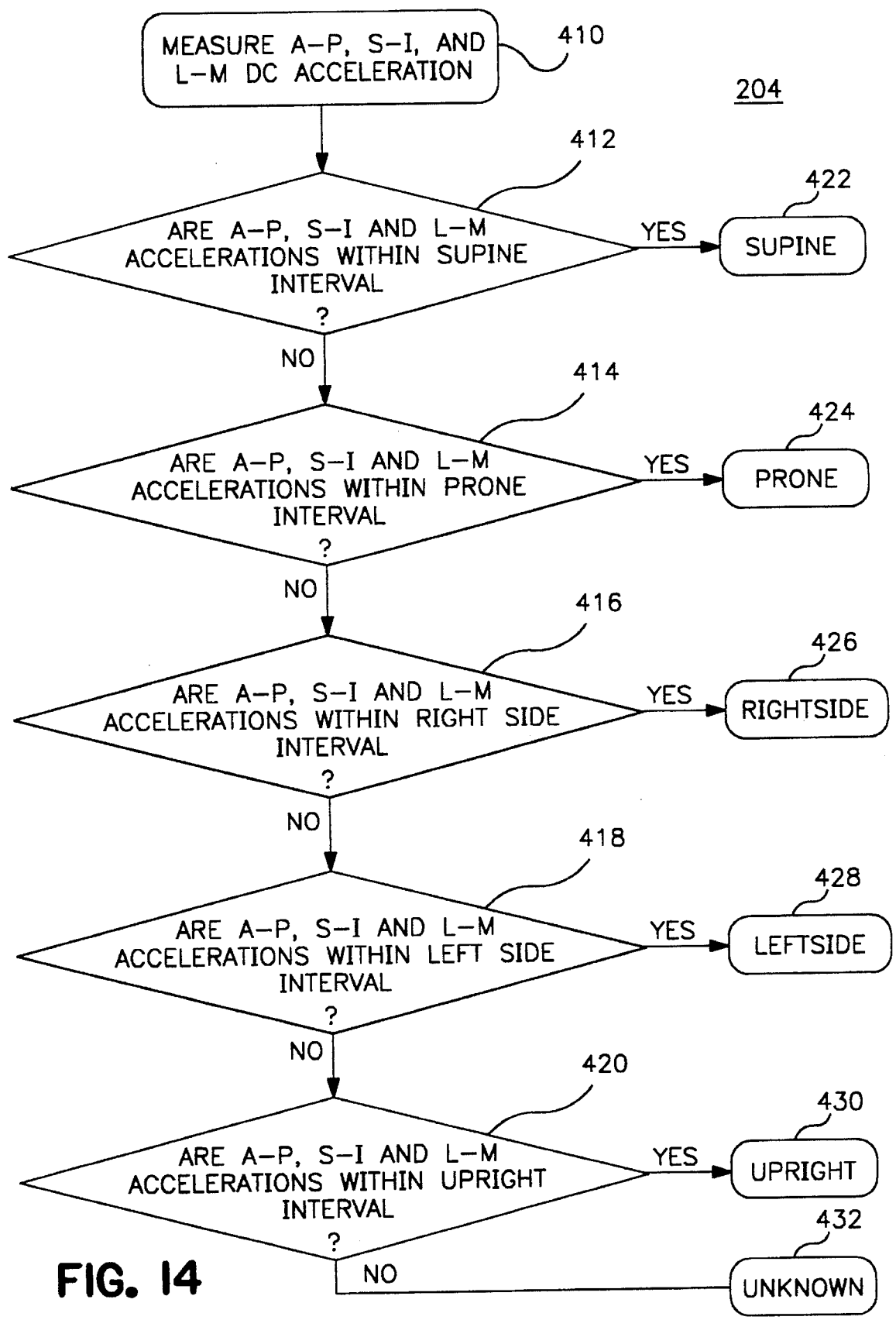
FIG. 14 is a flowchart of a second embodiment of the algorithm for determining body position from the DC components of the output signals of all three of the DC accelerometers of FIG. 2 employing the posture confidence intervals.

As mentioned above, it may be desirable to simplify the position determination and possibly increase the accuracy of determination by eliminating the +0.707 G and –0.707 G threshold signal levels and instead creating posture confidence windows or intervals that encompass the actual signal levels developed from each of two or three DC accelerometers used when the patient assumes the positions to be determined. FIG. 13 is a flow chart of a patient posture workup that may be undertaken to develop the posture confidence intervals. FIG. 14 is a flow chart of how the posture confidence intervals may be used by comparison with the sampled DC signal levels of the three DC accelerometers to determine the patient position in step 204 of FIG. 8.

In FIG. 13, the patient assumes a position, such as the supine position, in step 400. The DC acceleration is measured in that position in step 402 and used to create the posture confidence intervals in step 404. The procedure is repeated in step 406 until sets of posture confidence intervals are created for each body posture.

The posture confidence intervals may each constitute a range of signal levels on either side of the DC signal level measured from each DC accelerometer while the patient is in the assumed posture. For example, the signal levels corresponding to those generated by +0.25 G and –0.25 G acting on the sensitive axes of the DC accelerometers used when in the axis orientations to gravity depicted in FIGS. 4 or 5–7 may be added to the actual signal levels derived in step 402. Thus, for each posture, a set of two or three signal value threshold ranges are determined from the two or three measured DC acceleration signal levels. Each determined set is referred to as an interval related to the body posture, e.g. a supine interval, prone interval, rightside interval, leftside interval or upright interval (the patient is not subjected to the trivial case, upside down workup). The derived posture confidence intervals provide a higher confidence in the accuracy of the position determination and offset the misalignment of the IPG axes 82, 84, 86 to the patient's body axes 92, 94, 96 that may occur at implantation or over time.

The patient workup of FIG. 13 may therefore be conducted using the implanted IPG 30 to obtain the DC acceleration signal levels for the two or three sensitive axis DC accelerometers. The derived DC acceleration signals may be sampled and telemetered out to the external programmer 100 where the posture confidence intervals for each position are calculated. The calculated posture confidence intervals may then be programmed by telemetry into memory of the IPG 30. Alternatively, the IPG 30 may be commanded to make the calculations internally and to store the calculated posture confidence intervals.

FIG. 14 depicts the alternate embodiment of step 204 for declaring the patient's body position by comparing the measured DC acceleration signal levels against the posture confidence intervals. In step 410, the DC signal levels are measured as in step 310 above. In comparison steps 412–420, the measured DC acceleration intervals are compared to the posture confidence intervals. When a match is found, i.e., each measured signal level falls within the corresponding range, then the corresponding body posture of steps 422–430 is declared. If no match is found, then the body posture is declared unknown in step 432. Instances of unknown determination may be recorded in memory for telemetry out during subsequent physician examinations of the patient as a reliability check on the operating system. The posture confidence interval workup may be repeated from time to time to ensure that the migration of the IPG housing 70 is accounted for.

In a similar fashion as described above, posture confidence intervals may be derived for any selected pair of the S-I, A-P and L-M DC accelerometers and employed in such a comparison to determine the body posture. In such cases as exhibited in FIGS. 5–7 and 10–12, a greater number of positions are indeterminate than when using all three orthogonally disposed DC accelerometers 72, 74, 76.

Figure 15:
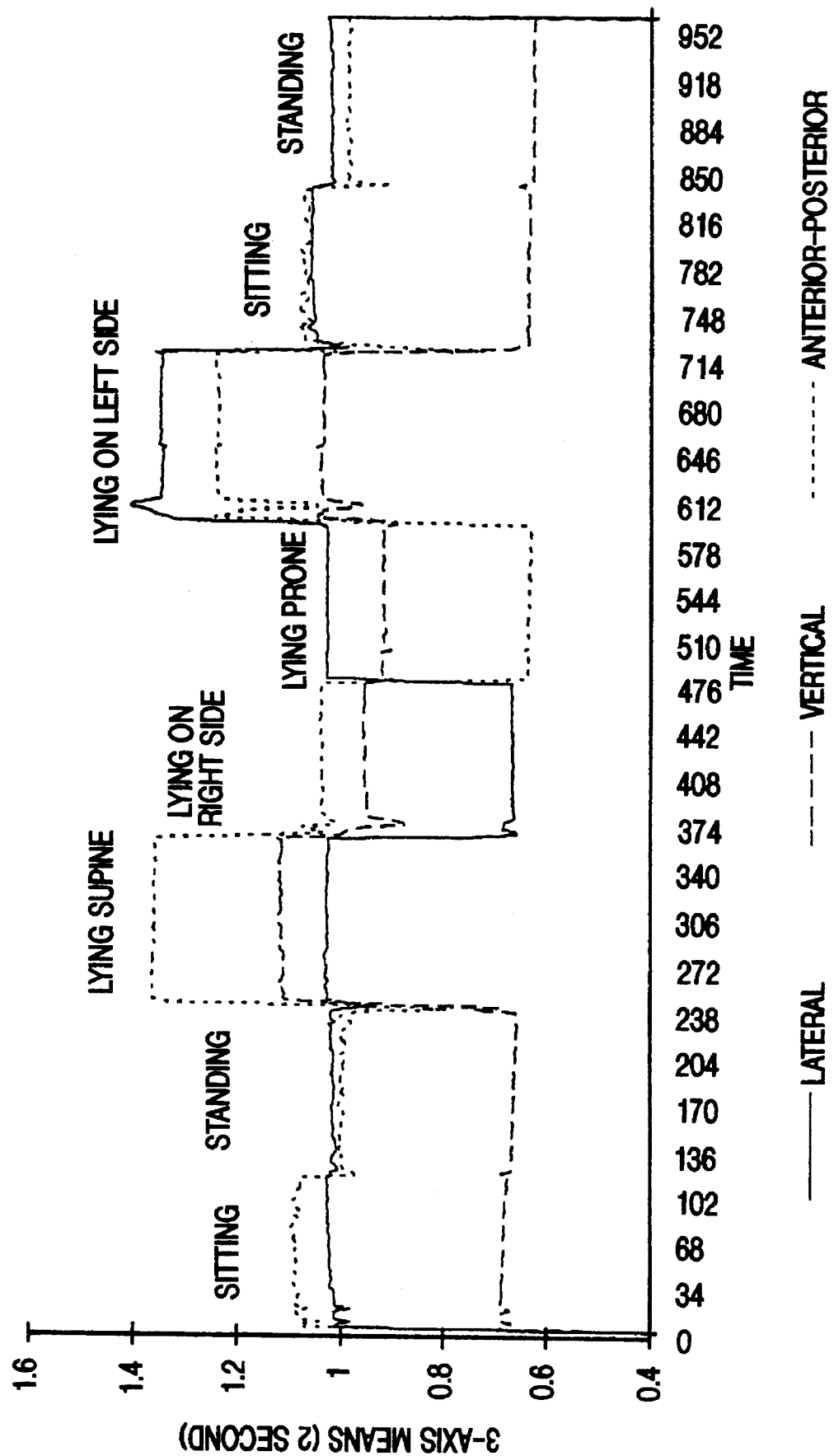
FIGS. 15 is a graph showing the DC accelerometer output signals obtained in different body positions.

FIG. 15 is a chart illustrating the mean voltage output or tilt signals collected in tests conducted employing a strap-on pulse generator housing of the type depicted in FIG. 2 with the orientations of the DC accelerometer sensitive axes and housing positional axes to the test subject's body axes as shown in FIG. 3. The two second mean voltage levels are depicted on a scale where 1.4 volts is generated in response to +1 G, 1.0 volts is generated at 0 G and 0.6 volts is generated in response to –1 G.

At an orientation of a sensitive axis at the –45° angle to the horizon used as a comparison threshold above, the accelerometer generates a mean voltage level of 0.72 volts on the scale of FIG. 15. Similarly, at an orientation of a sensitive axis at the +45° angle to the horizon used as a comparison threshold above, the accelerometer generates a mean voltage level of 1.28 volts on the scale of FIG. 15. The data depicted in FIG. 15 is derived over time in seconds as the test subject assumes the indicated positions. As can be seen from a comparison of the two second mean voltage levels, discrimination is possible between subject sitting, standing and lying prone, supine, and on either side.

Variations and modifications to the present invention may be possible given the above disclosure. Certain of the posture discrimination concepts developed herein may be employed with a single axis DC accelerometer to improve the discrimination function.

In addition, although the use of the two or three DC accelerometers are described above in relation to the determination of body posture for selecting a pacing rate, it will be understood that the present invention contemplates the use of the same in other therapeutic devices for delivering other therapies and in monitoring devices for storing body position alone or in relation to other monitored parameters. The present invention is also not limited to any particular pacing mode, and can function with prior art modes such as DDDR, AAIR, VVIR and DDIR. In addition, the detection of body position change from lying to an upright position may be used to set an appropriate transition pacing rate to treat syncopal patients susceptible to fainting.

It will also be understood that the present invention may be implemented in implantable tachyrhythmia control pacemakers, cardioverters, defibrillators and the like. Specifically, the enhanced capability of determining body position may be employed to augment detection of life threatening cardiac arrhythmias that render a patient prostrate. Determination that a patient is upright and active vs. prostrate may be useful in distinguishing a malignant tachyrhythmia from an appropriate or sinus tachycardia.

Furthermore, the present invention may be employed in sleep disorder or apnea monitors to record the body position during episodes. Similarly, the body position may be used to verify that a patient is lying down and likely asleep during an assumed sleep period of a circadian rhythm monitor or to augment a circadian rhythm algorithm for a treatment device.

All such variations and modifications are intended to be within the scope of the invention claimed by this letters patent.

I claim:

1. A method of determining the physical posture of a patient's body, having a superior-inferior body axis, an anterior-posterior body axis and a lateral-medial body axis, in relation to earth's gravitational field comprising the steps of:

implanting a multi-axis, solid state sensor, comprising first and second DC accelerometers having first and second sensitive axes, respectively, which respond to earth's gravitational field to provide first and second respective DC accelerometer signals of a magnitude and polarity dependent on the degree of alignment therewith, in the patient's body so that said first and second sensitive axes are generally aligned with a respective first and second one of said superior-inferior, anterior-posterior or lateral-medial body axes;

defining a first characteristic magnitude and polarity of said first and second DC accelerometer signals on alignment of the sensitive axes of said first and second DC accelerometers with earth's gravitational field, a second characteristic magnitude and polarity of said first and second DC accelerometer signals on alignment against earth's gravitational field, and a third characteristic magnitude and polarity of said first and second DC accelerometer signals on alignment normal to earth's gravitational field;

deriving first and second DC accelerometer signals from said first and second DC accelerometers as the patient assumes various body positions moving said first or second sensitive axes generally into alignment with earth's gravitational field; and determining the body posture of the patient through comparison of the magnitudes and polarities of said derived first and second DC accelerometer signals with the magnitudes and polarities of said first, second and third characteristic magnitudes and polarities.

2. The method of claim 1 further comprising the steps of:

defining a characteristic activity magnitude of said first and second DC accelerometer signals effected by body movement occurring within a predetermined frequency range signifying a threshold patient activity level; and deriving an activity level signal from said first or second DC accelerometer signals exceeding said characteristic activity magnitude over a predetermined time period.

3. The method of claim 2 further comprising the step of:

delivering a treatment therapy to the patient having a treatment parameter dependent on the determined body posture and the activity level signal of the patient.

4. The method of claim 2 further comprising the step of:

storing said determined body posture and activity level of the patient.

5. The method of claim 1 wherein said implanting step further comprises:

implanting said multi-axis, solid state sensor, comprising said first and second DC accelerometers having first and second sensitive axes, respectively, which respond to earth's gravitational field to provide first and second respective DC accelerometer signals of a magnitude and polarity dependent on the degree of alignment therewith, in the patient's body so that said first and second sensitive axes are generally aligned with said superior-inferior and one of said anterior-posterior and lateral-medial body axes, respectively.

6. The method of claim 1 wherein said implanting step further comprises:

implanting said multi-axis, solid state sensor, comprising said first and second DC accelerometers having first and second sensitive axes, respectively, which respond to earth's gravitational field to provide first and second respective DC accelerometer signals of a magnitude and polarity dependent on the degree of alignment therewith, in the patient's body so that said first and second sensitive axes are generally aligned with said anterior-posterior and lateral-medial body axes, respectively.

7. A method of determining the physical posture of a patient's body, having a superior-inferior body axis, an anterior-posterior body axis and a lateral-medial body axis, in relation to earth's gravitational field comprising the steps of:

implanting a multi-axis, solid state sensor, comprising first, second, and third DC accelerometers having first, second, and third sensitive axes, respectively, which respond to earth's gravitational field to provide first, second, and third respective DC accelerometer signals of a magnitude and polarity dependent on the degree of alignment therewith, in the patient's body so that said first, second and third sensitive axes are generally aligned with said superior-inferior, anterior-posterior and lateral-medial body axes, respectively;

defining a first characteristic magnitude and polarity of said first, second and third DC accelerometer signals on alignment of the sensitive axes of said first, second and third DC accelerometers with earth's gravitational field, a second characteristic magnitude and polarity of said first, second, and third DC accelerometer signals on alignment against earth's gravitational field, and a third characteristic magnitude and polarity of said first, second, and third DC accelerometer signals on alignment normal to earth's gravitational field;

deriving first, second, and third DC accelerometer signals from said first, second, and third DC accelerometers, respectively, as the patient assumes various body positions moving said first or second or third sensitive axes generally into alignment with earth's gravitational field; and determining the body posture of the patient through comparison of the magnitudes and polarities of said derived first, second, and third DC accelerometer signals with the magnitudes and polarities of said first, second and third characteristic magnitudes and polarities.

8. The method of claim 7 further comprising the steps of:

defining a characteristic activity magnitude of said first, second, and third DC accelerometer signals effected by body movement occurring within a predetermined frequency range signifying a threshold patient activity level; and deriving an activity level signal from said first or second or third DC accelerometer signals exceeding said characteristic activity magnitude over a predetermined time period.

9. The method of claim 8 further comprising the step of:

delivering a treatment therapy to the patient having a treatment parameter dependent on the determined body posture and the activity level signal of the patient.

10. The method of claim 8 further comprising the step of:

storing said determined body posture and activity level of the patient.

11. A method of pacing a patient's heart at a pacing rate dependent on patient activity and the physical posture of a patient's body, having a superior-inferior body axis, an anterior-posterior body axis and a lateral-medial body axis, in relation to earth's gravitational field, comprising the steps of:

measuring the constant acceleration of gravity on the patient's body in at least two of the superior-inferior, anterior-posterior, and lateral-medial body axes with first and second solid state DC accelerometer means aligned thereto for providing first and second DC accelerometer signals therefrom having a characteristic magnitude and polarity on alignment with earth's gravitational field and varying magnitude and polarity depending on the degree of mis-alignment of said first and second solid state DC accelerometer means with earth's gravitational field;

determining a body position signal related to the posture of the patient through comparison of the magnitudes and polarities of the first and second DC accelerometer signals with said characteristic magnitudes and polarities;

determining a patient activity signal from the frequency of body movements recurring over a time unit;

deriving a rate control signal from the body position and patient activity signals correlated to the physiologic demand on the patient's heart in the determined body posture and level of activity;

defining physiologic escape intervals as a function of the rate control signal to establish a physiologic pacing rate;

generating pacing pulses at the physiologic pacing rate; and applying the pacing pulses to a chamber of a patient's heart.

12. The method of claim 11 wherein said measuring step further comprises:

generally aligning the first and second sensitive axes of said first and second solid state DC accelerometers, respectively, with said superior-inferior body axis and one of said anterior-posterior and said lateral-medial body axes, respectively, and deriving said first and second DC accelerometer signals therefrom.

13. The method of claim 11 wherein said measuring step further comprises:

generally aligning the first and second sensitive axes of said first and second solid state DC accelerometers, respectively, with said lateral-medial and anterior-posterior body axes, respectively, and deriving said first and second DC accelerometer signals therefrom.

14. The method of claim 11 wherein said measuring step further comprises the steps of:

mounting a first solid state DC accelerometer having an first sensitive axis of deflection providing a first output signal varying in magnitude in response to the DC force of earth's gravitational field and AC forces of acceleration applied along the first sensitive axis in a pacemaker pulse generator housing so that the pulse generator may be implanted with the first sensitive axis generally aligned to a patient's superior-inferior body direction while in an upright posture;

mounting a second solid state DC accelerometer having an second sensitive axis of deflection providing a second output signal varying in magnitude in response to the DC force of earth's gravitational field and AC forces of acceleration applied along the second sensitive axis in said pacemaker pulse generator at a generally orthogonal angle to said first sensitive axis;

implanting said pulse generator in a patient's body such that said first sensitive axis is generally aligned with the patient's superior-inferior axis and said second axis is generally aligned with the patient's anterior-posterior or lateral-medial body direction while in the upright position; and deriving the first and second DC accelerometer signals from DC components of the first and second output signals; and said step of determining a body position signal related to the posture of the patient further comprises the steps of:

providing a reference DC accelerometer signal magnitude representative of the DC component of the first and second output signals generated by alignment of said first and second sensitive axes of said first and second DC accelerometers with the force of earth's gravitational field;

comparing the magnitudes of the first and second DC accelerometer signals to the reference DC accelerometer signal magnitude and determining from the comparison the position of the patient's body with respect to the force of earth's gravitational field; and providing the body position signal representative of the determined physical posture of the patient.

15. The method of claim 11 wherein said measuring step further comprises the steps of:

mounting a first DC accelerometer having an first sensitive axis of deflection providing a first output signal varying in magnitude in response to the DC force of earth's gravitational field and AC forces of acceleration applied along the first sensitive axis in a pacemaker pulse generator so that the pulse generator may be implanted with the first sensitive axis generally aligned to a patient's superior-inferior body axis while in an upright posture;

mounting a second DC accelerometer having an second sensitive axis of deflection providing a second output signal varying in magnitude in response to the DC force of earth's gravitational field and AC forces of acceleration applied along the second sensitive axis in said pacemaker pulse generator at a generally orthogonal angle to said first sensitive axis so that the pulse generator may be implanted with the second sensitive axis generally aligned to the patient's anterior-posterior body axis while in said upright posture;

mounting a third DC accelerometer having a third sensitive axis of deflection providing a third output signal varying in magnitude in response to the DC force of earth's gravitational field and AC forces of acceleration applied along the third sensitive axis in said pacemaker pulse generator at a generally orthogonal angle to said first and second sensitive axes so that the pulse generator may be implanted with the third sensitive axis generally aligned to the patient's lateral-medial body axis while in said upright posture;

implanting said pulse generator in a patient's body such that said first sensitive axis is generally aligned with the patient's superior-inferior axis and said second and third axes are generally aligned with the patient's anterior-posterior and lateral-medial body axes, respectively, while in said upright posture; and deriving the first, second and third DC accelerometer signals from DC components of the first, second, and third output signals; and said step of determining a body position signal related to the posture of the patient further comprises the steps of:

providing a reference DC accelerometer signal magnitude representative of the DC component of the first, second, and third output signal magnitudes generated by alignment of said first, second and third sensitive axes of said first, second and third DC accelerometers, respectively, with the force of earth's gravitational field;

comparing the magnitudes of the first, second and third DC accelerometer signals to the reference DC accelerometer signal magnitude and determining from the comparison the position of the patient's body with respect to the force of earth's gravitational field; and providing the body position signal representative of the determined posture of the patient.

16. Apparatus for determining the physical posture of a patient's body having patient body axes including a superior-inferior axis, an anterior-posterior axis and a lateral-medial axis by reference of the patient body axes to earth's gravitational field in an assumed body position comprising:

an implantable housing having first, second and third positional axes adapted to be implanted in a patient's body in a generally predetermined alignment relationship of said first, second and third positional axes with said superior-inferior, anterior-posterior, and lateral-medial body axes, respectively;

a first DC accelerometer mounted within said implantable housing having a first sensitive axis aligned with one of said first, second and third positional axes of said implantable housing for providing a first DC accelerometer signal varying in magnitude and polarity as a function of the degree of alignment of earth's gravitational field with or against said first sensitive axis in the body position assumed by the patient;

a second DC accelerometer mounted within said implantable housing having a second sensitive axis aligned with one other of said first, second and third positional axes of said implantable housing for providing a second DC accelerometer signal varying in magnitude and polarity as a function of the degree of alignment of earth's gravitational field with or against said second sensitive axis in the body position assumed by the patient; and means for determining the physical posture of the patient through a comparison of the magnitudes and polarities of said first and second DC accelerometer signals.

17. The apparatus of claim 16 further comprising means for determining the activity level of the patient from the frequency of body movements recurring over a time unit; and means for storing the determined physical posture and the activity level of the patient.

18. The apparatus of claim 16 further comprising:

means for delivering a treatment to the patient having a treatment parameter dependent on the body posture and the activity level of the patient.

19. The apparatus of claim 16 wherein said DC accelerometer means further comprises:

a first solid state DC accelerometer for measuring the constant acceleration of earth's gravitational field on the patient's body in the superior-inferior body axis and deriving said first DC accelerometer signal therefrom as the patient assumes various body positions moving said first or second or third sensitive axes generally into alignment with earth's gravitational field; and a second solid state DC accelerometer for measuring the constant acceleration of earth's gravitational field on the patient's body in one of the anterior-posterior and the lateral-medial body axes and deriving said second DC accelerometer signal therefrom as the patient assumes various body positions moving said first or second or third sensitive axes generally into alignment with earth's gravitational field.

20. The apparatus of claim 19 wherein said DC accelerometer means further comprises:

a third solid state DC accelerometer for measuring the constant acceleration of earth's gravitational field on the patient's body in the lateral-medial body axis and deriving a third DC accelerometer signal therefrom as the patient assumes various body positions moving said first or second or third sensitive axes generally into alignment with earth's gravitational field; and wherein:

said means for determining the posture of the patient is responsive to a comparison of a parameter of the first, second and third DC accelerometer signals.

21. The apparatus of claim 20 further comprising:

means for defining a first characteristic magnitude and polarity of said first, second and third DC accelerometer signals on alignment of the sensitive axes of said first, second and third DC accelerometers with earth's gravitational field, a second characteristic magnitude and polarity of said first, second, and third DC accelerometer signals on alignment against earth's gravitational field, and a third characteristic magnitude and polarity of said first, second, and third DC accelerometer signals on alignment normal to earth's gravitational field; and wherein:

said means for determining the posture of the patient is responsive to a comparison of the magnitudes and polarities of said derived first, second, and third DC accelerometer signals with the magnitudes and polarities of said first, second and third characteristic magnitudes and polarities.

22. The apparatus of claim 21 further comprising:

means for defining a characteristic activity magnitude of said first, second, and third DC accelerometer signals effected by body movement occurring within a predetermined frequency range signifying a threshold patient activity level; and means for deriving an activity level signal from said first or second or third DC accelerometer signals exceeding said characteristic activity magnitude over a predetermined time period.

23. The apparatus of claim 22 further comprising:

means for delivering a treatment therapy to the patient having a treatment parameter dependent on the determined body posture and the activity level signal of the patient.

24. The apparatus of claim 22 further comprising:

means for storing said determined body posture and activity level of the patient.

25. Apparatus for pacing a patient's heart at a pacing rate dependent on patient activity and the physical posture of a patient's body, having a superior-inferior body axis, an anterior-posterior body axis and a lateral-medial body axis, in relation to earth's gravitational field, comprising:

first and second solid state DC accelerometer means for measuring the constant acceleration of gravity on the patient's body in at least two of the superior-inferior, anterior-posterior, and lateral-medial body axes for providing first and second DC accelerometer signals therefrom having a characteristic magnitude and polarity on alignment with earth's gravitational field and varying magnitude and polarity depending on the degree of misalignment of said first and second solid state DC accelerometer means with earth's gravitational field;

means for determining a body position signal related to the posture of the patient through comparison of the magnitudes and polarities of the first and second DC accelerometer signals with said characteristic magnitudes and polarities;

means for determining a patient activity signal from the frequency of body movements recurring over a time unit;

means for deriving a rate control signal from the body position and patient activity signals correlated to the physiologic demand on the patient's heart in the determined body posture and level of activity;

means for defining physiologic escape intervals as a function of the rate control signal to establish a physiologic pacing rate;

means for generating pacing pulses at the physiologic pacing rate; and means for applying the pacing pulses to a chamber of a patient's heart.

26. The apparatus of claim 25 further comprising:

means for generally aligning the first and second sensitive axes of said first and second solid state DC accelerometers, respectively, with said superior-inferior body axis and one of said anterior-posterior and said lateral-medial body axes, respectively, and deriving said first and second DC accelerometer signals therefrom.

27. The apparatus of claim 25 further comprising:

means for generally aligning the first and second sensitive axes of said first and second solid state DC accelerometers, respectively, with said lateral-medial and anterior-posterior body axes, respectively, and deriving said first and second DC accelerometer signals therefrom.

28. The apparatus of claim 25 further comprising:

a pacemaker pulse generator housing;

means for mounting a first solid state DC accelerometer having a first sensitive axis of deflection providing a first output signal varying in magnitude in response to the DC force of earth's gravitational field and AC forces of acceleration applied along the first sensitive axis in said pacemaker pulse generator housing so that the pulse generator may be implanted with the first sensitive axis generally aligned to one of said patient's body axes while in an upright posture;

means for mounting a second solid state DC accelerometer having an second sensitive axis of deflection providing a second output signal varying in magnitude in response to the DC force of earth's gravitational field and AC forces of acceleration applied along the second sensitive axis in said pacemaker pulse generator at a generally orthogonal angle to said first sensitive axis;

said pacemaker pulse generator housing adapted to be implanted in the patients body such that said first sensitive axis is generally aligned with the selected one of the patient's body axes and said second axis is generally aligned with one of the other of the patient's body axes; and wherein:

said means for determining a body position signal related to the posture of the patient further comprises:

means for providing a reference DC accelerometer signal magnitude representative of the DC component of the first and second output signals generated by alignment of said first and second sensitive axes of said first and second DC accelerometers with the force of earth's gravitational field;

means for comparing the magnitudes of the first and second DC accelerometer signals to the reference DC accelerometer signal magnitude and determining from the comparison the position of the patient's body with respect to the force of earth's gravitational field; and means for providing the body position signal representative of the determined physical posture of the patient.

29. The apparatus of claim 25 further comprising:

a pacemaker pulse generator housing;

means for mounting a first DC accelerometer having an first sensitive axis of deflection providing a first output signal varying in magnitude in response to the DC force of earth's gravitational field and AC forces of acceleration applied along the first sensitive axis in a pacemaker pulse generator so that the pulse generator may be implanted with the first sensitive axis generally aligned to a patient's superior-inferior body axis while in an upright posture;

means for mounting a second DC accelerometer having an second sensitive axis of deflection providing a second output signal varying in magnitude in response to the DC force of earth's gravitational field and AC forces of acceleration applied along the second sensitive axis in said pacemaker pulse generator at a generally orthogonal angle to said first sensitive axis so that the pulse generator may be implanted with the second sensitive axis generally aligned to the patient's anterior-posterior body axis while in said upright posture;

means for mounting a third DC accelerometer having a third sensitive axis of deflection providing a third output signal varying in magnitude in response to the DC force of earth's gravitational field and AC forces of acceleration applied along the third sensitive axis in said pacemaker pulse generator at a generally orthogonal angle to said first and second sensitive axes so that the pulse generator may be implanted with the third sensitive axis generally aligned to the patient's lateral-medial body axis while in said upright posture;

said pacemaker pulse generator housing adapted to be implanted in a patient's body such that said first sensitive axis is generally aligned with the patient's superior-inferior axis and said second and third axes are generally aligned with the patient's anterior-posterior and lateral-medial body axes, respectively, while in said upright posture; and wherein:

said means for determining a body position signal related to the posture of the patient further comprises:

means for providing a reference DC accelerometer signal magnitude representative of the DC component of the first, second, and third output signal magnitudes generated by alignment of said first, second and third sensitive axes of said first, second and third DC accelerometers, respectively, with the force of earth's gravitational field;

means for comparing the magnitudes of the first, second and third DC accelerometer signals to the reference DC accelerometer signal magnitude and determining from the comparison the position of the patient's body with respect to the force of earth's gravitational field; and means for providing the body position signal representative of the determined posture of the patient.

* * * * *